US009949692B2

(12) United States Patent
Hunter

(10) Patent No.: US 9,949,692 B2
(45) Date of Patent: Apr. 24, 2018

(54) STENT GRAFT MONITORING ASSEMBLY AND METHOD OF USE THEREOF

(71) Applicant: William L. Hunter, Vancouver (CA)

(72) Inventor: William L. Hunter, Vancouver (CA)

(73) Assignee: Canary Medical Inc., Vancouver (CA)

( * ) Notice: Subject to any disclaimer, the term of this patent is extended or adjusted under 35 U.S.C. 154(b) by 0 days.

(21) Appl. No.: 14/654,529

(22) PCT Filed: Dec. 21, 2013

(86) PCT No.: PCT/US2013/077356
§ 371 (c)(1),
(2) Date: Jun. 20, 2015

(87) PCT Pub. No.: WO2014/100795
PCT Pub. Date: Jun. 26, 2014

(65) Prior Publication Data
US 2015/0335290 A1   Nov. 26, 2015

Related U.S. Application Data

(60) Provisional application No. 61/745,403, filed on Dec. 21, 2012.

(51) Int. Cl.
*A61F 2/06* (2013.01)
*A61B 5/00* (2006.01)
(Continued)

(52) U.S. Cl.
CPC .......... *A61B 5/6862* (2013.01); *A61B 5/0031* (2013.01); *A61B 5/01* (2013.01);
(Continued)

(58) Field of Classification Search
CPC ........... A61F 2/07; A61B 5/6862; A61B 5/02; A61B 5/026; A61B 5/4851
See application file for complete search history.

(56) References Cited

U.S. PATENT DOCUMENTS 6,053,873 A * 4/2000 Govari ................. A61B 5/0031
600/462
7,025,778 B2 * 4/2006 Hayashi ............. A61B 5/02014
623/1.16

(Continued)

FOREIGN PATENT DOCUMENTS

JP   2008237642   10/2008
WO  2005046467   5/2005
(Continued)

OTHER PUBLICATIONS

PCT International Search Report and Written Opinion or PCT/US2013/077356 dated May 9, 2014.

*Primary Examiner* — Brian Dukert
(74) *Attorney, Agent, or Firm* — BioMed IP

(57) ABSTRACT

Assemblies are provided for positioning within a lumen comprising a stent graft; and a sensor positioned on the stent graft. Within certain aspects the sensors are wireless sensors, and include for example one or more fluid pressure sensors, contact sensors, position sensors, pulse pressure sensors, blood volume sensors, blood flow sensors, chemistry sensors (e.g., for blood and/or other fluids), metabolic sensors (e.g., for blood and/or other fluids), mechanical stress sensors and/or temperature sensors.

18 Claims, 8 Drawing Sheets

(51) Int. Cl.
  *A61F 2/07* (2013.01)
  *A61B 5/01* (2006.01)
  *A61B 5/07* (2006.01)
  *A61B 5/0215* (2006.01)
  *A61B 5/145* (2006.01)
  *A61B 5/026* (2006.01)
  *A61B 5/06* (2006.01)

(52) U.S. Cl.
  CPC .............. *A61B 5/076* (2013.01); *A61F 2/07* (2013.01); *A61B 5/026* (2013.01); *A61B 5/0215* (2013.01); *A61B 5/02158* (2013.01); *A61B 5/065* (2013.01); *A61B 5/145* (2013.01); *A61B 5/14532* (2013.01); *A61B 5/14539* (2013.01); *A61B 5/14542* (2013.01); *A61B 5/14546* (2013.01); *A61B 2562/06* (2013.01); *A61F 2230/0069* (2013.01)

(56) References Cited

U.S. PATENT DOCUMENTS

| 7,416,530 | B2 * | 8/2008 | Turner | A61B 5/0031 600/485 |
|---|---|---|---|---|
| 2002/0128546 | A1 | 9/2002 | Silver | |
| 2008/0033527 | A1 * | 2/2008 | Nunez | A61B 5/0215 623/1.13 |

FOREIGN PATENT DOCUMENTS

| WO | 2007057739 | 5/2007 |
|---|---|---|
| WO | 2008006003 | 1/2008 |

* cited by examiner

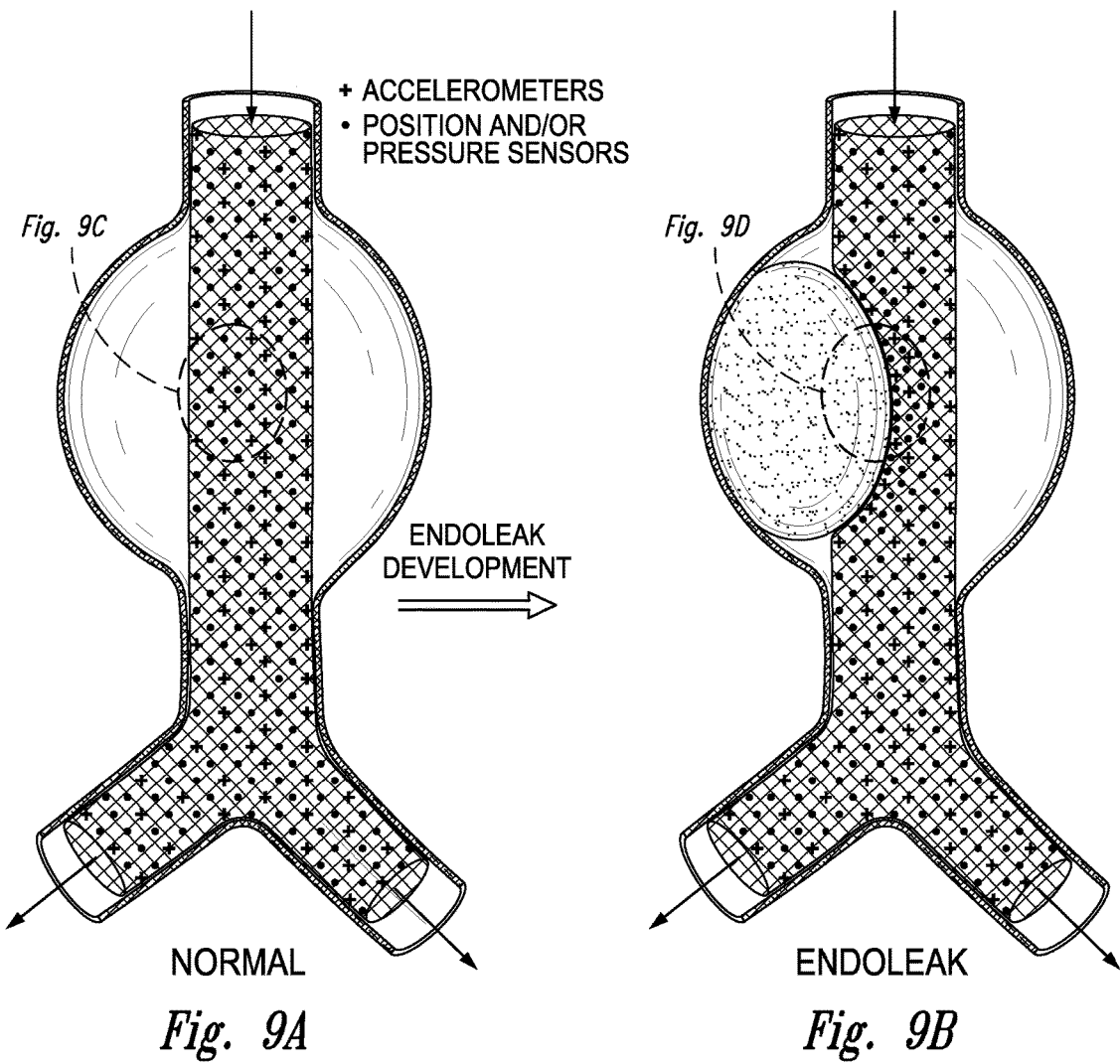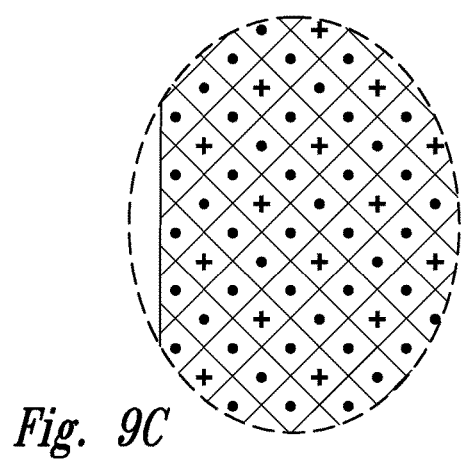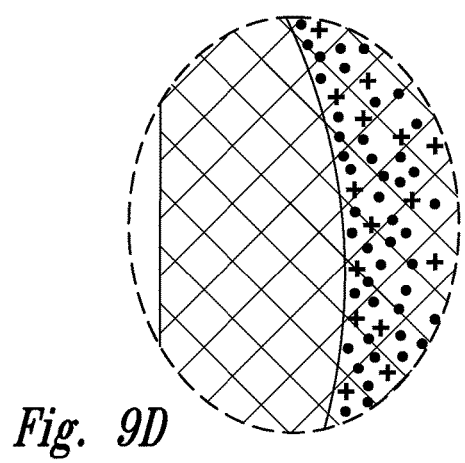
Fig. 9A  Fig. 9B  Fig. 9C  Fig. 9D

STENT GRAFT MONITORING ASSEMBLY AND METHOD OF USE THEREOF

CROSS-REFERENCE TO RELATED APPLICATION

This application is a national phase application under 35 U.S.C. § 371 of International Application No. PCT/US2013/077356, filed Dec. 21, 2013, which claims the benefit under 35 U.S.C. § 119(e) of U.S. Provisional Patent Application No. 61/745,403 filed Dec. 21, 2012, which application are incorporated herein by reference in their entirety.

FIELD OF THE INVENTION

The present invention relates generally to the field of stent grafts and, more particularly, to stent grafts for use in monitoring a variety of medical conditions, including for example endoleaks.

BACKGROUND

A stent graft is a tube composed of fabric generally supported by a polymeric or metallic structure. It can be used for a variety of conditions, most commonly in blood vessels to reinforce a weak spot in an artery, such as an aneurism. It may also be used in other locations, such as, for example, the esophagus. Typically, a stent graft is made of a radially expandable reinforcement structure, for example, a plurality of annular rings, and a cylindrically shaped layer of graft material. Representative examples of stent grafts include, for example, those disclosed in U.S. Pat. Nos. 6,123,722, 7,377,937, 7,691,141, 7,806,917, 7,914,568, 8,080,051 and 8,100,960.

The most common type of vascular stent graft is an endovascular stent graft used to treat an abdominal aortic aneurism or a thoracic aortic aneurism. The endovascular stent graft is placed inside the aneurysm and acts as a false lumen through which blood can travel, instead of flowing into the aneurysm sac, and is designed to help prevent an aneurism from bursting. Endovascular stent grafts are also used in dialysis grafts and dialysis fistulas to treat obstructions or aneurysms that occur at the site of vascular access required for hemodialysis treatments in kidney failure patients.

To perform endovascular stent graft implantations, a surgeon will insert the stent graft into the blood vessel at the location of the aneurism in order to reduce the pressure on the blood vessel walls at the site of the aneurism. Such stent grafts have been used widely for many years and are well known. Unfortunately, such endovascular stent grafts are sometimes subject to failure. One failure that may occur is leaking of blood into the aneurysm sac; a condition referred to as an endoleak, of which there are 5 different types. A Type I Endoleak occurs when blood flows between the stent graft and the blood vessel wall; typically at the proximal (often renal) or distal (often iliac) end of the graft. This complication may also occur as a result of movement of the graft away from the desired location, sometimes called migration. Type II Endoleaks occur when blood flows backwards (retrograde) into the aneurysm sac from arteries originating from the aneurysm sac itself (typically the lumbar, testicular or inferior mesenteric arteries). Type III endoleaks occur when blood leaks between the junction sites of "articulated" or "segmented" stent grafts; these multi-component stent grafts are inserted as separate segments which are then assembled inside the artery into their final configuration. Detecting and confirming accurate assembly and fluid-tight contact between the different segments is difficult and current verification methods of correct assembly are suboptimal. Type IV Endoleaks occur when cracks or defects develop in the stent graft fabric and blood is able to leak directly through the graft material. Lastly, Type V Endoleaks are leakage of blood into the aneurysm sac of an unknown origin. Regardless of their cause, endoleaks are frequently a medical emergency and early detection, characterization and monitoring of them is an important unmet medical need.

Other complications of stent graft placement include partial blockage of the blood flowing through the stent graft (stenosis), detachment, rupture, fabric wear (durability), kinking, malpositioning, and systemic cardiovascular disorders (myocardial infarction, congestive heart failure, arrhythmias, renal failure). Presently, detecting such complications prior to their occurrence or early in their development is difficult or, in many cases, impossible.

The present invention discloses novel stent grafts which overcome many of the difficulties of previous stent grafts, methods for constructing and utilizing these novel stent grafts, and further provides other related advantages.

SUMMARY

Briefly stated, stent grafts are provided with a number of sensors to monitor the integrity and efficaciousness of the stent graft, as well as to monitor the failure or impending failure of the stent graft due to a disease or other process (e.g., an endoleak). Representative stent grafts include, for example vascular (e.g., endovascular), gastrointestinal (e.g., esophageal), and urinary stent grafts.

Within one aspect of the invention an assembly for positioning within a lumen is provided, comprising a stent graft and a sensor positioned on the stent graft. Within the context of the present invention, the term "Assembly" or "Assemblies", and "Sensor-Containing Stent Graft" are utilized to refer to the stent graft (or a portion thereof) which has one or more of the sensors provided herein. In addition, use of the term "Stent Graft" should also be understood to mean a stent graft having one or more sensors, as required by the context of such usage.

Within various embodiments of the invention, one or more sensors may be positioned anywhere in, on or within the stent graft, including for example on the outer (adluminal) wall, the inner (luminal) wall, between the inner and outer walls of the stent graft, or, any combinations of these. Within further embodiments the sensor(s) can be positioned on the luminal surface, adluminal surface, implanted within the vascular wall of the aneurysm, or any combination of these. Within related embodiments the sensor comprises a multiplicity or plurality of sensors (optionally, different types of sensors) which can be positioned on and/or within multiple surfaces of the stent graft and the vascular wall of the aneurysm, or within the aneurysm itself.

Various sensors may be utilized herein, including for example fluid pressure sensors, contact sensors, position sensors, pulse pressure sensors, blood volume sensors, blood flow sensors, chemistry sensors (e.g., for blood and/or other fluids), metabolic sensors (e.g., for blood and/or other fluids), accelerometers, mechanical stress sensors, temperature sensors, and the like. Within certain embodiments, the sensor is a wireless sensor. Within yet other embodiments the sensor is connected to a wireless microprocessor. Within a further embodiment the sensor is passive and thus does not require its own power supply.

Within various embodiments a plurality of the aforementioned sensors are positioned on the stent graft, and within preferred embodiments, the stent graft can contain more than one type of sensor (e.g., one or more of, or any combination of the following: fluid pressure sensors, contact sensors, position sensors, pulse pressure sensors, blood volume sensors, blood flow sensors, chemistry sensors (e.g., for blood and/or other fluids), metabolic sensors (e.g., for blood and/or other fluids), accelerometers, mechanical stress sensors, temperature sensors, and the like).

Within other aspects of the invention, the stent graft comprises two or more segments. Within preferred embodiments sensors are provided which sense joining of the two or more segments.

Within further embodiments, the stent graft can contain sensors at specified densities in specific locations. For example, the stent graft can have a density of sensors is greater than 1 sensor per square centimeter, 2, 3, 4, 5, 6, 7, 8, 9, or 10 or greater sensors per square centimeter, or if calculated on a volume basis, greater than 1, 2, 3, 4, 5, 6, 7, 8, 9 or 10 sensors per cubic centimeter of the stent graft. (e.g., fluid pressure sensors, contact sensors, position sensors, pulse pressure sensors, blood volume sensors, blood flow sensors, chemistry sensors (e.g., for blood and/or other fluids), metabolic sensors (e.g., for blood and/or other fluids), accelerometers, mechanical stress sensors, temperature sensors, or any combination of these). Within related embodiments, the sensors (e.g., fluid pressure sensors, contact sensors, position sensors, pulse pressure sensors, blood volume sensors, blood flow sensors, chemistry sensors (e.g., for blood and/or other fluids), metabolic sensors (e.g., for blood and/or other fluids), accelerometers, mechanical stress sensors and temperature sensors) can be positioned at particular locations on or within the stent graft, including for example, the proximal and/or terminal one, two, or three centimeters of the device, and/or within portions of the device which are to be connected (e.g., the connecting segments of an articulating stent graft; for example, the main body of a AAA stent graft and the adjoining segment arm).

Within certain embodiments of the invention, the stent graft is provided with a specific unique device identifying number ("UDI"), and within further embodiments, each of the sensors on the graft each have either a specific unique sensor identification number ("USI"), or a unique group identification number ("UGI", e.g., an identification number that identifies the sensor as one of a group of sensors such as a fluid pressure sensor, contact sensor, position sensor, pulse pressure sensor, blood volume sensor, blood flow sensor, blood chemistry sensor, blood metabolic sensor, and/or mechanical stress sensor). Within yet further embodiments, the USI is specifically associated with a position on the stent graft.

Within various embodiments, the stent grafts provided herein may be utilized to provide data which identifies a number of different conditions or diseases, including development of a type I, II, III, IV and/or V endoleak. Moreover, the stent graft may additional provide specific cardiac measurements, including for example, the cardiac output, stroke volume, ejection fraction, systolic and/or diastolic blood pressure, mean arterial pressure, systemic vascular resistance, and total peripheral resistance. The stent graft may also be utilized to measure and record temperature changes within the blood and/or vascular walls of a subject.

Within other aspects of the invention methods are provided for monitoring a stent graft comprising the steps of transmitting a wireless electrical signal from a location outside the body to a location inside the body; receiving the signal at a sensor positioned on a stent graft located inside the body; powering the sensor using the received signal; sensing data at the sensor; and outputting the sensed data from the sensor to a receiving unit located outside of the body.

The integrity of the stent graft can be wirelessly interrogated and the results reported on a regular basis. This permits the health of the patient to be checked on a regular basis or at any time as desired by the patient and/or physician.

Within further embodiments, each of the sensors contains a signal-receiving circuit and a signal output circuit. The signal-receiving circuit receives an interrogation signal that includes both power and data collection request components. Using the power from the interrogation signal, the sensor powers up the parts of the circuitry needed to conduct the sensing, carries out the sensing, and then outputs the data to the interrogation module. The interrogation module acts under control of a control unit which contains the appropriate I/O circuitry, memory, a controller in the form of a microprocessor, and other circuitry in order to drive the interrogation module. Within yet other embodiments the sensor (e.g., fluid pressure sensor, contact sensor, position sensors, pulse pressure sensor, blood volume sensor, blood flow sensor, blood chemistry sensor, blood metabolic sensor, and/or mechanical stress sensor) are constructed such that they may readily be sewn into or otherwise mechanically attached to the stent graft (e.g., by way of a an opening or other appendage that provides permanent attachment of the sensor to the stent graft).

Within yet other aspects of the invention methods devices are provided suitable for transmitting a wireless electrical signal from a location outside the body to a location inside the body; receiving the signal at one of the aforementioned sensors positioned on a stent graft located inside the body; powering the sensor using the received signal; sensing data at the sensor; and outputting the sensed data from the sensor to a receiving unit located outside of the body. Within certain embodiments the receiving unit can provide an analysis of the signal provided by the sensor.

The details of one or more embodiments are set forth in the description below. The features illustrated or described in connection with one exemplary embodiment may be combined with the features of other embodiments. Other features, objects and advantages will be apparent from the description, the drawings, and the claims. In addition, the disclosures of all patents and patent applications referenced herein are incorporated by reference in their entirety.

BRIEF DESCRIPTION OF THE DRAWINGS

FIG. 9 illustrates the development of an endoleak from the beginning of the leak (9A) to substantial formation of the leak (9B). FIGS. 9C and 9D are a blown up images of 9A and 9B, respectively, which depicts the movement of various sensors during development of the endoleak.

DETAILED DESCRIPTION OF THE INVENTION

Figure 1:
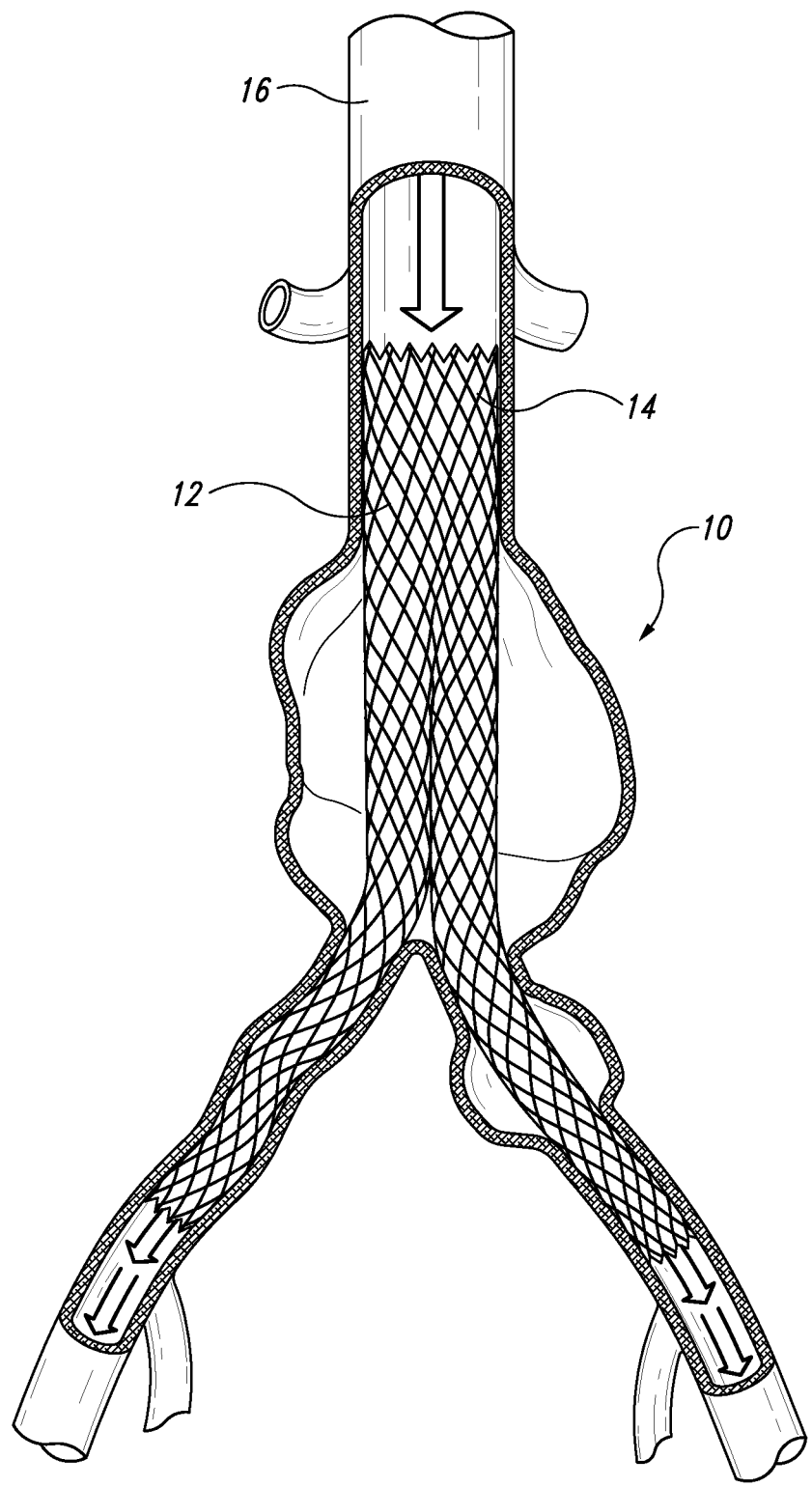
FIG. 1 is a schematic illustration of an abdominal aortic aneurism with a stent graft positioned therein.

As noted above, stent grafts are provided with a number of sensors to monitor the integrity and efficaciousness of the stent graft, as well as to monitor the failure or impending failure of the stent graft due to a disease or other process (e.g., an endoleak). Prior to setting forth the invention however, it may be helpful to an understanding thereof to first set forth definitions of certain terms that are used hereinafter.

"Stent graft" refers to a device comprising a graft or covering (composed of a textile, polymer, or other suitable material such as biological tissue) which maintains the flow of fluids (e.g., blood or lymph) from one portion of a vessel to another, and an endovascular scaffolding or stent (including expandable and balloon-inflatable stent structures) that holds open a body passageway and/or supports the graft or covering. Endovascular stent grafts may be used to treat a variety of vascular conditions, including treating abdominal aortic aneurysms and thoracic aortic aneurysms (referred to as "EVAR"—endovascular aortic aneurysm repair), atherosclerosis, peripheral vascular disease or other vascular diseases. Endovascular stent grafts are also used in dialysis grafts and dialysis fistulas to treat obstructions or aneurysms that occur at the site of vascular access in hemodialysis patients. Non-vascular stent grafts can be used in a variety of other body passageways such as the esophagus, colon, bile duct, urethra and ureter to name a few examples. Within certain embodiments, the stent graft has at least two openings (and within further embodiments, three or more openings), an outer (adluminal) surface, and an inner (luminal) surface. Within certain embodiments the stent graft is an "articulated" or "segmented" stent graft; these multi-component stent grafts are inserted as separate segments which are then assembled inside the body (artery or other body passageway) into their final configuration. Within other embodiments, the stent graft is fenestrated (e.g. FEVAR—fenestrated endovascular aortic aneurysm repair) with holes in the graft body material that maintain the patency of important blood vessels (or side branches). With certain embodiments, the stent graft has a Unique Device Identification ("UDI") number.

"Sensor" refers to a device that can be utilized to measure one or more different aspects of a body, of a stent graft inserted within a body, and/or the integrity, impact, efficaciousness or effect of the stent graft inserted within a body. Representative examples of sensors suitable for use within the present invention include, for example, fluid pressure sensors, contact sensors, position sensors, pulse pressure sensors, blood volume sensors, blood flow sensors, chemistry sensors (e.g., for blood and/or other fluids), metabolic sensors (e.g., for blood and/or other fluids), accelerometers, mechanical stress sensors and temperature sensors. Within certain embodiments the sensor can be a wireless sensor, or, within other embodiments, a sensor connected to a wireless microprocessor. Within further embodiments one or more (including all) of the sensors can have a Unique Sensor Identification number ("USI") which specifically identifies the sensor.

A wide variety of sensors (also referred to as Microelectromechanical Systems or "MEMS", or Nanoelectromechanical Systems or "NEMS", and BioMEMS or BioNEMS, see generally https://en.wikipedia.org/wiki/MEMS) can be utilized within the present invention. Representative patents and patent applications include U.S. Pat. No. 7,383,071 and U.S. Publication No. 2010/0285082. Representative publications include "Introduction to BioMEMS" by Albert Foch, CRC Press, 2013; "From MEMS to Bio-MEMS and Bio-NEMS: Manufacturing Techniques and Applications by Marc J. Madou, CRC Press 2011; "Bio-MEMS: Science and Engineering Perspectives, by Simona Badilescu, CRC Press 2011; "Fundamentals of BioMEMS and Medical Microdevices" by Steven S. Saliterman, SPIE—The International Society of Optical Engineering, 2006; "Bio-MEMS: Technologies and Applications", edited by Wanjun Wang and Steven A. Soper, CRC Press, 2012; and "Inertial MEMS: Principles and Practice" by Volker Kempe, Cambridge University Press, 2011; Polla, D. L., et al., "Microdevices in Medicine," Ann. Rev. Biomed. Eng. 2000, 02:551-576; Yun, K. S., et al., "A Surface-Tension Driven Micropump for Low-voltage and Low-Power Operations," *J. Microelectromechanical Sys.*, 11:5, October 2002, 454-461; Yeh, R., et al., "Single Mask, Large Force, and Large Displacement Electrostatic Linear Inchworm Motors," *J. Microelectromechanical Sys.*, 11:4, August 2002, 330-336; and Loh, N. C., et al., "Sub-10 cm$^3$ Interferometric Accelerometer with Nano-g Resolution," *J. Microelectromechanical Sys.*, 11:3, June 2002, 182-187; all of the above of which are incorporated by reference in their entirety.

In order to further understand the various aspects of the invention provided herein, the following sections are provided below: A. Stent Grafts and Their Use; B. Representative Embodiments of Stent Grafts; C. Use of Stent grafts to Deliver Desired Agent(s); D. Methods for Monitoring Infection in Stent grafts; E. Further Uses of Sensor-containing Stent grafts in Healthcare; F. Generation of Power from Stent grafts; G. Medical Imaging and Self-Diagnosis of Assemblies Comprising Stent grafts, Predictive Analysis and Predictive Maintenance; H. Methods of Monitoring Assemblies Comprising Stent grafts; and I. Collection, Transmission, Analysis, and Distribution of Data from Assemblies Comprising Stent grafts.

A. Stent Grafts and their Use

As noted above, stent grafts are typically utilized in a wide variety of medical procedures to open up and/or maintain the lumen of a body passageway (e.g. artery, gastrointestinal tract, urinary tract). They are most commonly used however for vascular procedures, e.g., in the treatment of aortic aneurysm disease. An aortic aneurysm AA) is a dilatation of the aorta that usually results from underlying disease (typically atherosclerosis) causing weakness in the vessel wall. As the aneurysm progressively grows in size over time, the risk of it bursting or rupturing rapidly increases; a condition which if not promptly treated, leads to massive hemorrhage and death. Stent grafts are inserted into an aneurysm, not only to simply hold open the diseased vessel, but also to bridge across the dilated vascular segment from healthy vessel to healthy vessel.

Briefly, a stent graft is inserted over a guide wire, from the femoral or iliac artery and deployed within the aneurysm, resulting in maintenance of blood flow from an aorta of acceptable (usually normal) caliber above the aneurysm to a portion of aorta or iliac artery(s) of acceptable (usually normal) caliber below the aneurysm. The aneurysm sac is thus excluded from the circulation. Blood within the excluded aneurysm sac thromboses and thus has no flow within it, presumably reducing the pressure and thus its tendency to burst.

Presently available stent grafts, however, have a number of limitations such as endoleaks, migration, detachment, wear and durability issues, rupture, stenosis, kinking and malpositioning. For example, current stent grafts are prone to persistent leakage around the area of the stent graft and into the aneurysm sac (a condition known as an "endoleak"). Hence, pressure within the aneurysm sac is not reduced, stays at or near arterial pressure, and is still at risk for rupture. Endoleaks are among the most common and the most clinically dangerous complications of stent graft placement and the early detection and treatment of endoleaks remains a significant medical problem. Stent grafts of the present invention have, within certain embodiments, pressure detecting sensors that are able to detect elevated pressure within the aneurysm sac and warn the patient and/or the attending physician that there may be a potential endoleak. Pressure sensors at the ends of the stent graft and located throughout the body of the stent graft (on or within the fabric and/or metallic scaffold) can recognize adluminal (the outer surface of the graft in contact with the blood vessel wall) pressure rising; this is suggestive that pressure within the aneurysm sac is becoming elevated and that the aneurysm is no longer excluded from the circulation. Within other embodiments pressure sensors can be implanted onto or into the aneurysm wall itself during stent graft placement. Since most endoleaks are asymptomatic to the patient (rupture is often the first symptom), a gradual or rapid increase in stent graft adluminal pressure (or aneurysm wall pressure) is an important early indicator that medical care should be sought and that investigation into its underlying cause is warranted. Currently, there is no such continuous monitoring and early detection system available to recognize endoleaks and embodiments of the present invention will greatly facilitate the identification and early treatment of this potentially fatal complication of stent graft treatment.

There are 5 common types of perigraft leakage (endoleak), and corrective measures can vary depending upon the underlying cause. Stent grafts of the present invention have, within certain embodiments, fluid pressure sensors, contact sensors, position sensors, pulse pressure sensors, blood volume sensors, blood flow sensors, chemistry sensors (e.g., for blood and/or other fluids), metabolic sensors (e.g., for blood and/or other fluids), accelerometers, mechanical stress sensors, temperature sensors, and the like, which are capable of providing information useful to the physician for determining which type of endoleak might be present.

The first type of endoleak (Type I Endoleak) occurs when there is direct leakage of blood around the stent graft (either proximally or distally) and into the aneurysm sac. This type of endoleak can be persistent from the time of insertion because of poor sealing between the stent graft and vessel wall, or can develop later because the seal is lost. In addition, this problem can develop due to changes in the position or orientation of the stent graft in relation to the aneurysm as the aneurysm grows, shrinks, elongates or shortens with time after treatment. Type I endoleaks also commonly occur if the stent graft "migrates downstream" from its initial point of placement as a result of being shifted distally by the flow of blood and arterial pulsations. Representative stent grafts can have contact and/or position sensors concentrated at the proximal and distal ends of the stent graft (as well as within the body of the stent graft) to assist in the identification of a Type I endoleak. Stent grafts equipped with pressure and contact sensing devices can indicate the suspected presence of an endoleak through the detection of elevated adluminal pressure; furthermore loss of contact with the vessel wall (as detected by the contact sensors) at the proximal and/or distal ends of the graft would suggest the presence of a Type I endoleak, while loss of contact of the body of the stent graft with the vessel wall would suggest the location, size and extent of the endoleak present in the aneurysm sac. Lastly, position sensors and/or accelerometers concentrated at the proximal and/or distal ends of the stent graft (as well as in the body of the stent graft) can detect movement (migration) of the stent graft from its original point of placement (a common cause of Type I Endoleaks) and also aid in determining the size and location of the endoleak (by detecting deformations of the stent graft wall).

As noted above, within certain embodiments of the invention specific sensors can be identified by their USI, as well as by their positional location within the stent graft. Hence, a more comprehensive image or analysis of the overall function of the stent graft (and of the patient's response to the stent graft) can be ascertained based upon knowledge of the location and activities of a group of sensors collectively. For example, a collection of sensors, when analyzed as a group could be utilized to ascertain the specific type of endoleak, the degree and the location of the endoleak. In addition, the collection of sensors could be utilized to assess a variety of other conditions, including for example, kinking or deformation of the stent graft, and stenosis of the stent graft.

Figure 10:
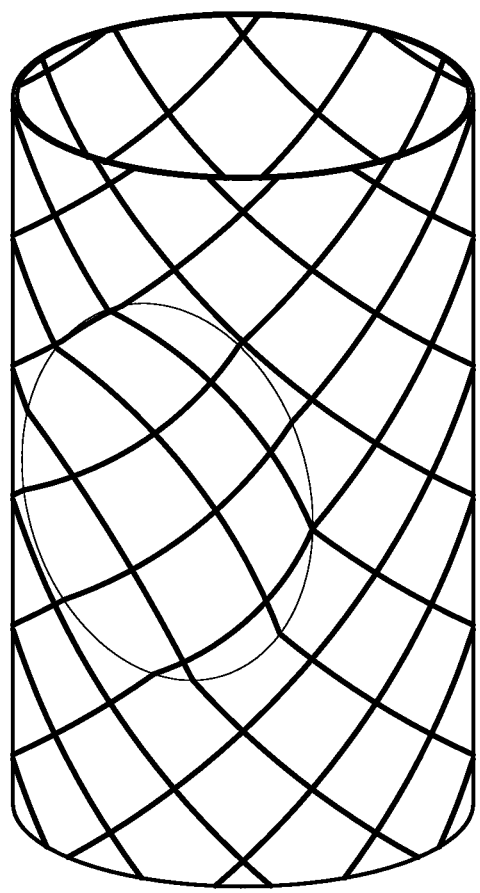
FIG. 10 illustrates the formation of an endoleak in three dimensions.

One such example of a collection of sensors which can be interrogated as a group is shown in FIGS. 9 and 10. More specifically, FIG. 9A shows development of an endoleak, which eventually becomes more complete (FIG. 9B). As shown in the blown-up images (FIGS. 9C and 9D), dues to the endoleak sensors will be moved from their typical specified position (whether uniform or designed), to a different position. The movement, rate of movement, pressure, and other metrics of measurement (depending upon the type of sensor) can be interrogated at a single time point, as well as over a time course. Moreover, as shown in FIG. 10, the three-dimensional spacial deformation of the stent (and four-dimensional if time is also considered), may be determined based upon the movement, pressure, and other metrics of the sensors.

The collection of data from the sensors can also be utilized to ensure proper placement of the stent graft (e.g., that no leaks are present at the time of placement), and that the stent graft is appropriately positioned (e.g., and that the side arm is appropriately attached to the main body of the stent graft).

The second type of perigraft leak (Type II Endoleak) can occur because there are side arteries extending out the treated segment of blood vessel (typically the lumbar arteries, testicular arteries and/or the inferior mesenteric artery). Once the aneurysm is excluded by the stent graft, flow can reverse within these blood vessels and continue to fill the aneurysm sac around the stent graft. Representative stent grafts can have contact and/or position sensors concentrated at the proximal and distal ends of the stent graft (as well as within the body of the stent graft) to assist in the identification of a Type II endoleak. Stent grafts equipped with pressure and contact sensing devices can indicate the suspected presence of an endoleak through the detection of elevated adluminal pressure; furthermore continued contact with the vessel wall (as detected by the contact sensors) at the proximal and/or distal ends of the graft would suggest the endoleak could be a Type II, while loss of contact of the body of the stent graft with the vessel wall would suggest the location, size and extent of the endoleak present in the aneurysm sac. Lastly, position sensors and/or accelerometers concentrated at the proximal and distal ends of the stent graft would confirm that the stent graft had not migrated from its original point of placement, while those in the body of the stent graft would aid in determining the size and anatomical location of the endoleak (by detecting deformations of the stent graft wall) which could suggest the blood vessel responsible for the Type II endoleak.

The third type of endoleak (Type III Endoleak) can occur because of disarticulation of the device (in the case of modular or segmented devices). Due to the complicated vascular anatomy, the diversity of aneurysm shapes and the need to custom fit the stent graft to a particular patient, many stent grafts are composed of several segments that are inserted separately and constructed within aorta into their final configuration. Disarticulation of the device at the junction points can develop due to changes in shape of the aneurysm as it grows, shrinks, elongates or shortens with time after treatment. Representative segmented stent grafts can have contact and/or position sensors concentrated at the articulation points of the stent graft to assist in assessing the integrity of the seal between stent graft segments. During placement of the stent graft, complimentary (paired/matched) contact sensors on the respective articulated segments can confirm that a precise and accurate connection has been achieved during construction of the device. Should a Type III endoleak develop, gaps/discontinuities between contact sensors on complimentary segments can be detected to ascertain both the location and extent of the endoleak present.

A fourth type of endoleak (Type IV Endoleak) occurs due to the development of holes within the graft material through which blood can leak into the aneurysm sac. Continuous pulsation of the vessel causes the graft material to rub against the metallic stent tynes eventually leading to fabric wear and graft failure. Representative stent grafts have fluid pressure sensors, contact sensors, position sensors, pulse pressure sensors, blood volume sensors, blood flow sensors, chemistry sensors (e.g., for blood and/or other fluids), metabolic sensors (e.g., for blood and/or other fluids), accelerometers, mechanical stress sensors, temperature sensors, and the like sensors on and/or within the fabric of the body of the stent graft to assist in the identification of a Type IV endoleak. Should a defect develop in the graft material, the embedded sensors will aid in determining the size and location of the endoleak by detecting deformations and defects of the stent graft wall. In extreme cases, stent graft wall defects can lead to rupture of the stent graft; a condition that can be detected early as a result of embodiments of this invention.

The final type of endoleak (Type V Endoleak) is a leak of unknown origin. Representative stent grafts equipped with fluid pressure sensors, contact sensors, position sensors, pulse pressure sensors, blood volume sensors, blood flow sensors, chemistry sensors (e.g., for blood and/or other fluids), metabolic sensors (e.g., for blood and/or other fluids), accelerometers, mechanical stress sensors, temperature sensors, and the like can indicate the suspected presence of an endoleak through the detection of elevated adluminal pressure. Furthermore, loss of contact with the vessel wall detected by contact sensors, changes in position sensors and/or movements detected by accelerometers can detect changes in the stent graft and assist in determining the size and location of the endoleak (by detecting deformations of the stent graft wall).

The integration of data from the fluid pressure sensors, contact sensors, position sensors, pulse pressure sensors, blood volume sensors, blood flow sensors, chemistry sensors (e.g., for blood and/or other fluids), metabolic sensors (e.g., for blood and/or other fluids), accelerometers, mechanical stress sensors, temperature sensors, and the can produce a computer reconstruction of the stent graft wall that can serve a function similar to medical "imaging" of the device (see e.g., FIGS. 9 and 10). Stent grafts of the present invention, within certain embodiments, can provide sensing information to serve a variety of important clinical functions.

For example, this information is useful to the clinician during initial placement of the stent graft to determine if it is correctly placed anatomically, if there is leakage around the graft, if stent graft segments are correctly assembled, to detect kinking or deformation of the graft, to ascertain if there is uniform blood flow through the device—to name but a few important functions. Malpositioning of the stent graft, either at the time of placement or due to subsequent movement/migration, is a common complication of stent graft therapy. Sensor-containing stent grafts of the present embodiment can be used to confirm proper initial placement and any ensuing relocation. Detachment of the graft as a whole (from the artery), or detachment of individual graft segments from each other is another problematic complication of stent graft insertion and ongoing therapy. Stent grafts of the present invention have the ability to detect movement/detachment of the entire stent graft, as well as movement and/or detachment of individual segments, providing the clinician and patient with valuable diagnostic information. Kinking of the stent graft during deployment and/or as the result of subsequent movement after placement is also a significant clinical problem if it develops. Stent grafts of the present invention have position sensors and accelerometers distributed throughout the stent graft capable of detecting deformation and kinking of the stent graft.

In some cases, the lumen of the stent graft can become narrowed and restrict blood flow through the graft due to external compression (such as an endoleak), stenosis (the growth of thickened vascular tissue called neointimal hyperplasia on the inner surface of the stent graft), or the formation of a blot clot. Stent grafts of the present invention have a variety of sensors capable of detecting and differentiating types of stenosis. Blood flow, fluid pressure and blood volume sensors located on the luminal surface are able to detect the presence and location of a stenosis due to the increased blood flow speed and increased blood (and pulse) pressure at the site of a stenosis (relative to normal segments of the graft). Stenosis due to external compression (such as the presence of an endoleak as discussed above). Stenosis due to neointimal hyperplasia or clot formation will be detected as "dead spots" and/or altered readings on the luminal surface as blood flow sensors, blood metabolic and/or chemistry sensors (e.g., for blood and/or other fluids) become covered by vascular tissue or clot; while adluminal pressure sensors and accelerometers will not show changes in adluminal pressure or stent graft wall deformation (as would occur with an endoleak). Metabolic sensors and chemistry sensors are capable of determining the difference between stenosis (normal pH and physiologic readings) and clot (lowered pH and altered physiologic readings).

As mentioned, stent grafts are often placed in arteries (typically the aorta) in anatomic locations where important arterial side branches originate. Of greatest importance are the renal arteries, but the lumbar, testicular, inferior mesenteric and internal iliac arteries can be affected by an aortic aneurysm. To maintain patency of these arteries (and prevent them from being obstructed by the placement of the stent graft), stent grafts with holes (or fenestrations) have been developed that allow blood flow through the graft and into the arteries that branch out from the aorta. FEVAR (fenestrated endovascular aortic aneurysm repair) is a form stent graft design and treatment that maintains the patency of important blood vessels that originate from the aorta. Stent grafts of the present invention have blood flow sensors, fluid pressure sensors, pulse pressure sensors, blood volume sensors and/or blood chemistry and metabolic sensors at the fenestration sites to monitor blood flow through the side branches. Stent grafts of the present invention may also have position sensors, contact sensors and/or accelerometers at the fenestration sites to monitor patency of the side branches (due to stenosis and/or kinking, migration and obstruction of the arterial branches by the stent graft itself).

In addition, patients requiring stent grafts often have extensive cardiovascular disease resulting in impaired cardiac and circulatory function. For example, patients receiving stent grafts are at an increased risk for myocardial infarction (heart attack), congestive heart failure, renal failure and arrhythmias. The aorta is the largest blood vessel to originate from the heart; therefore, monitoring certain hemodynamic and metabolic parameters within the aorta can provide the clinician with very important information regarding the patient's cardiac, renal and circulatory function. Stent grafts of the present invention contain fluid pressure sensors, contact sensors, position sensors, pulse pressure sensors, blood volume sensors, blood flow sensors, chemistry sensors (e.g., for blood and/or other fluids), metabolic sensors (e.g., for blood and/or other fluids), accelerometers, mechanical stress sensors, temperature sensors, and the like, suitable for such purposes. Representative stent grafts of the present invention can have pressure sensors, pulse pressure sensors, pulse contour sensors, blood volume sensors, blood flow sensors on and/or within the stent graft which can be used by one of ordinary skill in the art to calculate and monitor important physiologic parameters such as cardiac output (CO), stroke volume (SV), ejection fraction (EV), systolic blood pressure (sBP), diastolic blood pressure (dBP), mean arterial pressure (mAP), systemic vascular resistance (SVR), total peripheral resistance (TPV) and pulse pressure (PP). For example, the FloTrac/Vigileo (Edwards Life Sciences, Irvine, Calif.) uses pulse contour analysis to calculate stroke volume (SV) and systemic vascular resistance (SVR); the pressure recording analytical method (PRAM) is used by Most Care (Vytech, Padora, Italy) to estimate cardiac output (CO) from analysis of the arterial pressure wave profile. Changes in cardiac output (CO), stroke volume (SV) and ejection fraction (EF) and cardiac index (CI) can be an important in detecting complications such myocardial ischemia and infarction; they can also assist the clinician in implementation and adjusting cardiac medications and dosages. Pulse pressure sensors, pulse contour sensors and heart rate sensors contained on and within stent grafts of the present invention can assist in the detection and monitoring of cardiac arrhythmias and heart rate abnormalities; they too can be used to monitor the patient's response to cardiac medications that effect heart rate and rhythm. Systolic blood pressure (sBP), diastolic blood pressure (dBP), mean arterial pressure (mAP), systemic vascular resistance (SVR) and total peripheral resistance (TPV) readings can be used by the clinician to monitor the dosage and effect of blood pressure lowering medications and pressor (blood pressure increasing) agents.

As described above, patients requiring stent grafts often have concurrent medical problems related to cardiovascular disease such as renal impairment or renal failure. The renal arteries originate from the aorta, often in close approximation to the typical location of stent graft placement; therefore, monitoring certain hemodynamic and metabolic parameters within the aorta can provide the physician and patient with very important "real time" information regarding ongoing renal function. Stent grafts of the present invention can contain circulatory sensors (as described herein) as well as chemistry sensors (e.g., for blood and/or other fluids) and metabolic sensors (e.g., for blood and/or other fluids) suitable for monitoring kidney function. Examples of blood chemistry and metabolic sensors of utility for this embodiment include, but are not limited to, Blood Urea Nitrogen (BUN), Creatinine (Cr) and Electrolytes (Calcium, Potassium, Phosphate, Sodium, etc). Furthermore, combining metabolic data with hemodynamic data and urinalysis can allow the clinician to calculate the Glomerular Filtration Rate (GFR) which is a very useful measure of kidney function. This information would be of particular utility in the management of dialysis patients to monitor the timing, effectiveness, and frequency of dialysis therapy.

Finally, due to the numerous complications described above, there is long term uncertainty about the entire stent graft technology as a treatment for aortic aneurysm. Although much more invasive and traumatic, standard open surgical aneurysm repair is extremely durable and effective. Uncertainties about endovascular stent grafts include whether they will lower the aneurysm rupture rate, rate of perigraft leak (endoleak), device migration, ability to effectively exclude aneurysms over a long term, and device rupture or disarticulation. Stent grafts of the present invention, with their ability to detect and monitor many (if not all) of the aforementioned complications, are an important advancement of stent graft therapy as a whole.

B. Representative Embodiments of Stent Grafts

FIG. 1 illustrates an abdominal aortic aneurism 10 of the type which may occur in patients. A stent graft 12 has been positioned inside the aneurism 10 to form a stent graft 14 in physical contact with a blood vessel wall 16. While such stent grafts are beneficial to reduce pressure in the aneurism sac and significantly increase the health of the patient, sometimes difficulties occur in which the stent graft, including for example, various types of endoleaks. Five types of endoleaks are commonly known and labeled Type I-Type V. A Type I Endoleak occurs when blood flows between the stent graft and the blood vessel wall; typically at the proximal (often renal) or distal (often iliac) end of the graft. This complication may also occur as a result of movement or migration of the graft away from the site of implantation. Type II Endoleaks occur when blood flows backwards (retrograde) into the aneurysm sac from arteries originating from the aneurysm sac itself (typically the lumbar, testicular or inferior mesenteric arteries). Type III endoleaks occur when blood leaks between the junction sites of "articulated" or "segmented" stent grafts; these multi-component stent grafts are inserted as separate segments which are then assembled inside the artery into their final configuration. Type IV Endoleaks occur when cracks or defects develop in the stent graft fabric and blood is able to leak directly through the graft material, while Type V endoleaks are of an unknown origin.

In order to monitor the health of the patient, it is desirable to identify any one of the five types of endoleaks (discussed above) which may occur in a stent graft. In addition, it is desirable to monitor cardiac output, blood flow, blood volume, and various characteristics of the blood internal to the stent graft.

Figure 4:
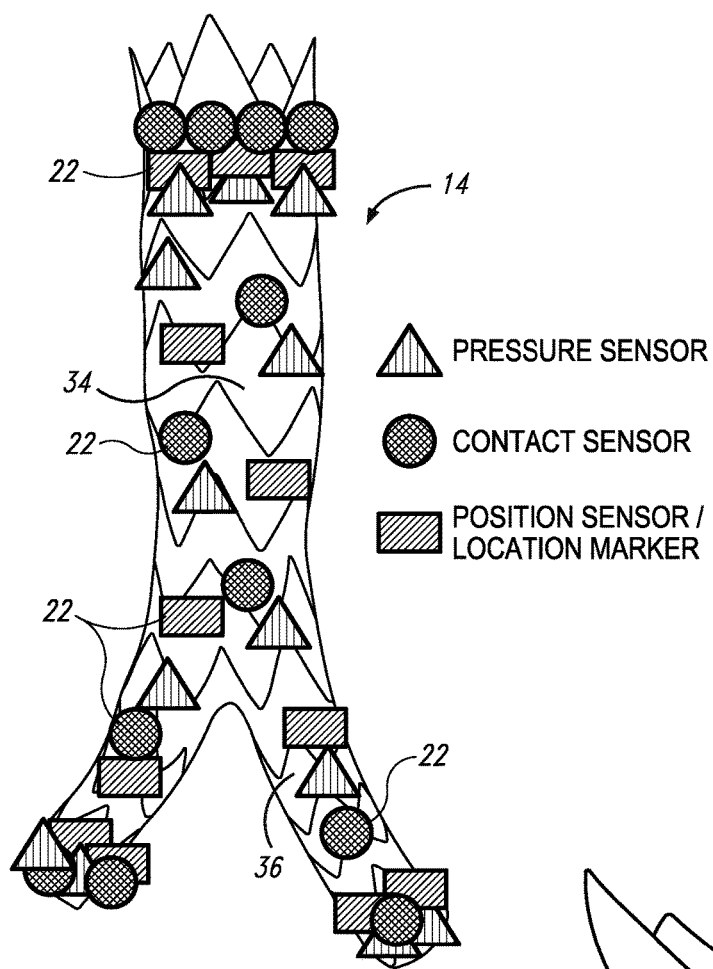
FIG. 4 is a schematic illustration of a plurality of sensors that can be placed along outer portions of a stent graft.

FIG. 4 illustrates different types of sensors that may be positioned on the outer wall of the stent graft in order to sense various conditions of the stent graft relative to the blood vessel, and the status of the aneurism. As illustrated in FIG. 4, it may include one or more pressure sensors located at the proximal and distal ends of the stent graft, as well as within the aneurism sac in order to sense the fluid pressure at various locations along the outer wall of the stent graft and within the aneurism sac. Additionally, it may include one or more contact sensors at the distal end of the stent graft, the proximal end of the stent graft, and various locations along the stent graft to determine whether the stent is in physical contact with the blood vessel wall. The contact sensors may be of a type of physical pressure sensors, whereas the pressure sensors are fluid pressure sensors. In addition, one or more position markers are located on the stent graft to determine whether or not it has moved relative to the blood vessel wall, since movement of the stent graft is one of the conditions which causes failure. It should also be noted that the sensors can also be implanted directly onto or into the aneurysm wall as part of the procedure to implant the stent graft into the patient.

Figure 5:
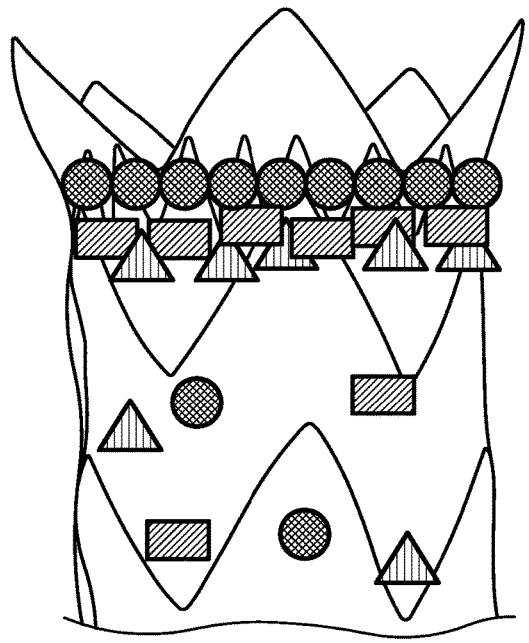
FIG. 5 is a schematic illustration of an enlarged view of a proximal end of the stent graft showing, within one embodiment the locations of a variety of sensors.

FIG. 5 is an enlarged view of the proximal end of the stent graft of FIG. 4 showing the large numbers of sensors that can be positioned at critical locations, such as at the proximal end where a sealing contact with the blood vessel is preferred for proper operation of the stent graft.

Figure 6:
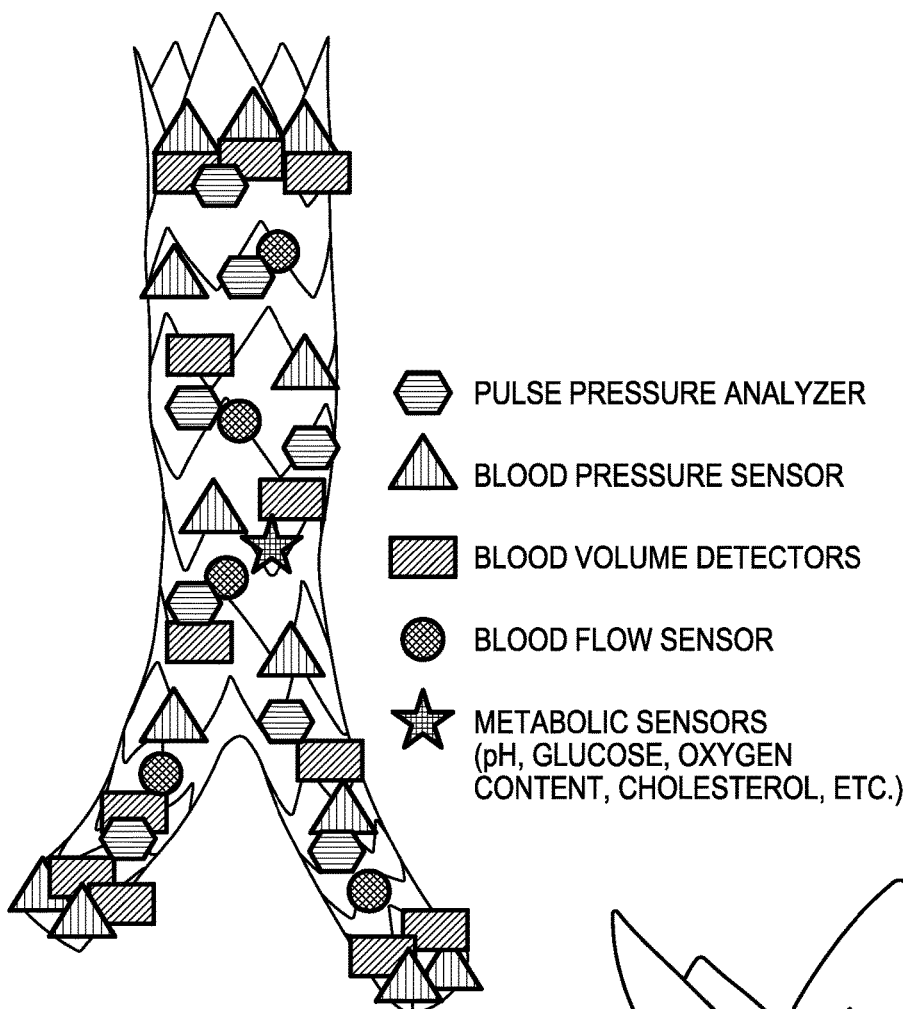
FIG. 6 is a schematic illustration of a plurality of sensors on the inner wall of a stent graft.
Figure 7:
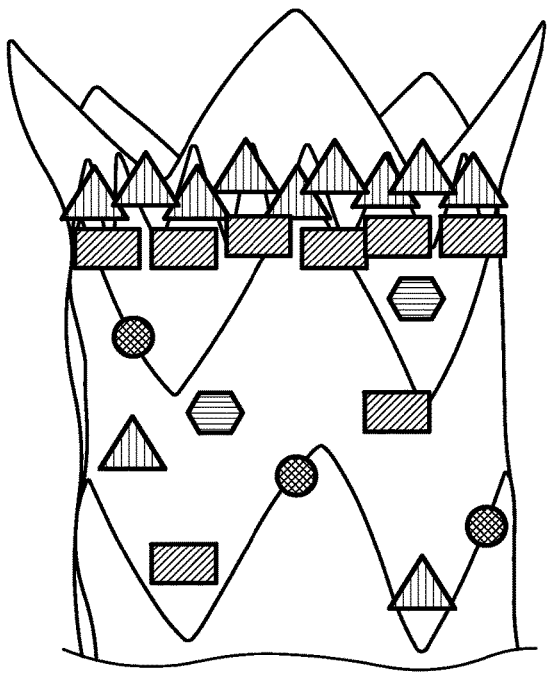
FIG. 7 is a schematic illustration of an enlarged view of the proximal end of a stent graft showing a plurality of sensors thereon.

FIGS. 6 and 7 illustrate a variety of sensors on the inner wall of the stent graft and in between layers of the fabric that form the stent. Some of the sensors are positioned in a location exposed to the blood flowing through the stent graft. The sensors which are on the inner wall of the stent graft can both monitor the integrity of the stent graft and also the properties of the blood flowing through the stent graft. Accordingly, the sensors on the inside surface of the stent graft may include a pulse analyzer to determine the pulse properties of the patient. It may also include a plurality of blood pressure sensors to sense the blood pressure of the patient inside the lumen. It may also include both blood flow and blood volume detectors to sense the cardiac output of the patient. In addition, the stent graft provides an excellent location in order to determine various blood properties, such as the pH, the glucose level, the oxygen content, the cholesterol level, and other properties inside the blood as it flows through the stent. Thus, as shown in FIG. 6, a variety of different sensors can be placed on the inner wall of the stent graft in order to sense for both the integrity of the stent graft as well as the blood flowing through the stent. Some of the sensors shown in FIG. 6 may include sensors woven into the fabric of the stent or positioned between the various layers of fabric that make up the stent. For example, such sensors may include stress sensors that sense the amount of stress being placed on the fabric of the sensor a various locations. The sensors may also include pressure sensors to sense local mechanical pressure of the various layers of fabric that make up the stent.

The sensors used can also include accelerometers and motion sensors to detect movement of the stent graft due to heart beats or other physical changes. Changes in the position of the accelerometers and/or motion sensors over time can be used as a measurement of changes in the position of the stent graft wall and/or vascular wall over time. Such positional changes can be used as a surrogate marker of vascular and stent graft anatomy—i.e. they can form an "image" of the stent graft and/or vascular wall to provide information on the size, shape and location of endoleaks, kinking of the stent graft, disarticulation of a segmented stent graft, stenosis with the stent graft, clot formation, and/or stent graft movement/migration.

FIG. 7 is an enlargement of the proximal end of the stent graft showing the location of various sensors which can perform sensing functions both for the integrity of the stent graft and the blood properties of the patient.

C. Use of Stent Grafts to Deliver Desired Agent(s)

As noted above, the present invention also provides drug-eluting stent grafts and drug-coated stent grafts which comprise one or more sensors, and which can be utilized to release a desired agent (e.g., a drug) to a desired location within the body (e.g., a body lumen, an aneurysm sac, and/or vessel walls). Within related embodiments, a drug-eluting delivery device may be included within the stent graft in order to release a desired drug upon demand (e.g., upon remote activation/demand, or based upon a timed schedule, see generally U.S. Patent App. No. 2011/0092948 entitled "Remotely Activated Piezoelectric Pump For Delivery of Biological Agents to the Intervertebral Disc and Spine", which is incorporated by reference in its entirety), or upon detection of an activating event (e.g., detection of a leak by a pressure sensor). For example, within certain embodiments of the invention biological agents can be administered along with or released from a stent graft in order to increase fibrosis or scarring within an aneurysm sac. Representative examples of suitable agents include, for example, irritants, silk, wool, talcum powder, metallic beryllium, and silica. Other agents which may be released by the stem graft include components of extracellular matrix, fibronectin, polylysine, ethylenevinylacetate, and inflammatory cytokines such as TGFβ, PDGF, VEGF, bFGF, TNFα, NGF, GM-CSF, IGF-a, IL-1, IL-8, IL-6, and growth hormone, and adhesives such as cyanoacrylate (see U.S. Patent App. Nos. 2004/0199241, 2005/0171594, 2005/0177103, 2005/0181004, 2005/0186242, 2005/0149173, 2005/0021126 and 2006/0192214, all of which are incorporated by reference in their entirety).

Within other embodiments of the invention anti-scarring biological agents (e.g., drugs such as paclitaxel, sirolimus, or an analog or derivative of these), can be administered along with or released from a stent graft in order to prevent scarring of the implant inappropriately (see, e.g., U.S. Pat. No. 7,491,188, U.S. Patent Application Nos. 2005/0152945, 2005/0187639, 2005/051871, 2006/055088, 2006/0079836, US 2009/0254063, US 2010/0023108, and US 2010/0042121).

Within preferred embodiments one or more sensors (e.g., pressure sensors, contact sensors, and/or position sensors) can be utilized to determine appropriate placement of the desired drug, as well as the quantity and release kinetics of drug to be released at a desired site.

D. Methods for Monitoring Infection

Within other embodiments stent grafts are provided comprising one or more temperature sensors. Such stent grafts can be utilized to measure the temperature of blood, vessel wall, the stent graft, and in the local tissue and environment adjacent to the stent graft. Methods are also provided for monitoring changes in temperature over time, in order to determine and/or provide notice (e.g., to a patient and/or a healthcare provider) that an infection may be imminent.

In certain embodiments of the present invention, metabolic and physical sensors can also be placed on or within the stent graft or various components of a stent graft in order to monitor for rare, but potentially life-threatening complications. In some patients, the stent graft and surrounding tissues can become infected. Sensors such as temperature sensors (detecting temperature increases), pH sensors (detecting pH decreases), and other metabolic sensors can be used to suggest the presence of infection on or around the stent graft. For example, temperature sensors may be included on or within a stent graft in order to allow early detection of infection, and preemptive treatment with antibiotics or surgical intervention.

E. Further Uses of Sensor-Containing Stent Grafts in Healthcare

Sensors on stent grafts, and any associated medical device has a variety of benefits in the healthcare setting, and in non-healthcare settings (e.g., at home or work). For example, postoperative progress can be monitored (readings compared from day-to-day, week-to-week, etc.) and the information compiled and relayed to both the patient and the attending physician allowing rehabilitation to be followed sequentially and compared to expected (typical population) norms. Within certain embodiments, a wearable device interrogates the sensors on a selected or randomized basis, and captures and/or stores the collected sensor data. This data may then be downloaded to another system or device (as described in further detail below).

Integrating the data collected by the sensors described herein (e.g., contact sensors, position sensors, strain gauges and/or accelerometers) with simple, widely available, commercial analytical technologies such as pedometers and global positioning satellite (GPS) capability, allows further clinically important data to be collected such as, but not restricted to: extent of patient ambulation (time, distance, steps, speed, cadence), patient activity levels (frequency of activity, duration, intensity), exercise tolerance (work, calories, power, training effect), range of motion (discussed later) and stent graft performance under various "real world" conditions. It is difficult to overstate the value of this information in enabling better management of the patient's recovery. An attending physician (or physiotherapist, rehabilitation specialist) only observes the patient episodically during scheduled visits; the degree of patient function at the exact moment of examination can be impacted by a multitude of disparate factors such as: the presence or absence of pain, the presence or absence of inflammation, time of day, compliance and timing of medication use (pain medications, anti-inflammatories), recent activity, patient strength, mental status, language barriers, the nature of their doctor-patient relationship, or even the patient's ability to accurately articulate their symptoms—to name just a few. Continuous monitoring and data collection can allow the patient and the physician to monitor progress objectively by supplying objective information about patient function under numerous conditions and circumstances, to evaluate how performance has been affected by various interventions (pain control, anti-inflammatory medication, rest, etc.), and to compare patient progress versus previous function and future expected function. Better therapeutic decisions and better patient compliance can be expected when both the doctor and the patient have the benefit of observing the impact of various treatment modalities on patient rehabilitation, activity, function and overall performance.

F. Generation of Power

Within certain aspects of the invention, one or more small electrical generation units can be positioned inside, within, and/or upon of the stent graft. Briefly, a variety of techniques have been described for scavenging power from small mechanical movements or mechanical vibration. See, for example, the article entitled "Piezoelectric Power Scavenging of Mechanical Vibration Energy," by U. K. Singh et al., as published in the Australian Mining Technology Conference, Oct. 2-4, 2007, pp. 111-118, and the article entitled "Next Generation Micro-power Systems by Chandrakasan et al., as published in the 2008 Symposium on VLSI Circuits Digest of Technical Papers, pp. 1-5. See also U.S. Pat. No. 8,283,793 entitled "Device for Energy Harvesting within a Vessel," and U.S. Pat. No. 8,311,632 entitled "Devices, Methods and Systems for Harvesting Energy in the Body," all of the above of which are incorporated by reference in their entirety. These references provide examples of different types of power scavengers which can produce electricity from very small motion and store the electricity for later use. The above references also describes embodiments in which pressure is applied and released from the particular structure in order to produce electricity without the need for motion, but rather as a result of the application of high pressure. In addition, these references describe embodiments wherein electricity can be produced from pulsatile forces within the body.

After the electricity is generated by one or more generators, the electricity can be transmitted to any one of the variety of sensors which is described herein. For example, it can be transmitted to the sensors 22 shown in the Figures. It may also be transmitted to the other sensors described herein. The transmission of the power can be carried out by any acceptable technique. For example, if the sensor is physically coupled to the stent graft, electric wires may run from the generator to the particular sensor. Alternatively, the electricity can be transmitted wirelessly in the same way that wireless smartcards receive power from closely adjacent power sources using the appropriate send and receive antennas. Such send and receive techniques of electric power are also described in the publication and the patent applications and issued U.S. patent previously described, all of which are incorporated herein by reference.

G. Medical Imaging and Self-Diagnosis of Assemblies Comprising Stent Grafts; Predictive Analysis and Predictive Maintenance Within other aspects of the invention methods are provided for imaging the stent graft as provided herein, comprising the steps of (a) detecting the location of one or more sensors in the stent graft, and/or associated medical device; and (b) visually displaying the location of said one or more sensors, such that an image of the stent graft and/or medical device is created. Within various embodiments, the step of detecting may be done over time, and the visual display may thus show positional movement over time. Within certain preferred embodiments the image which is displayed is a three-dimensional image. Within other embodiment, the imaging techniques may be utilized post-operatively in order to examine the stent graft, and/or to compare operation and/or movement of the device over time.

The present invention provides stent grafts which are capable of imaging through the use of sensors over a wide variety of conditions. For example, within various aspects of the invention methods are provided for imaging the stent graft (or portion thereof) with sensors, comprising the steps of detecting the changes in sensors in, on, and or within the stent graft, medical device or kit over time, and wherein the stent graft, medical device or kit comprises sensors at a density of greater than 1, 2, 3, 4, 5, 6, 7, 8, 9, 10 or greater than 10 sensors per square centimeter. Within other aspects the stent graft medical device or kit comprises sensors at a density of greater than 1, 2, 3, 4, 5, 6, 7, 8, 9, 10 or greater than 10 sensors per cubic centimeter. Within either of these embodiments there can be less than 50, 75, 100, or 100 sensors per square centimeter, or per cubic centimeter. Within various embodiments the at least one or more of the sensors may be placed randomly, or at one or more specific locations within the stent graft, medical device, or kit as described herein. As noted above, a wide variety of sensors can be utilized therein, including for example, contact sensors, strain gauge sensors, pressure sensors, fluid pressure sensors, position sensors, pulse pressure sensors, blood volume sensors, blood flow sensors, blood chemistry sensors, blood metabolic sensors, mechanical stress sensors, and temperature sensors.

For example, the stent graft comprising sensors as described herein can be utilized to image anatomy through sensors which can detect positional movement. The sensors used can also include accelerometers and motion sensors to detect movement of the stent graft due to a variety of physical changes. Changes in the position of the accelerometers and/or motion sensors over time can be used as a measurement of changes in the position of the stent graft over time. Such positional changes can be used as a surrogate marker of stent graft anatomy—i.e. they can form an "image" of the stent graft to provide information on the size, shape and location of changes to the stent graft, and/or stent graft movement/migration. Representative embodiments of such image are provided in FIGS. 9 and 10.

Certain exemplary embodiments will now be explained in more detail. One particular benefit is the live and in-situ monitoring of the patient's recovery with a stent graft implant as shown in FIG. 9. The sensors as described herein are collecting data on a constant basis, during normal daily activities and even during the night if desired. For example, the contact sensors can obtain and report data once every 10 seconds, once a minute, or once a day. Other sensors will collect data more frequently, such as several times a second. For example, it would be expected that the temperature, contact, and/or position data could be collected and stored several times a second. Other types of data might only need to be collected by the minute or by the hour. Still other sensors may collect data only when signaled by the patient to do so (via an external signaling/triggering device) as part of "event recording"—i.e. when the patient experiences a particular event (e.g. pain, injury, etc.)—and signals the device to obtain a reading at that time in order to allow the comparison of subjective/symptomatic data to objective/sensor data in an effort to better understand the underlying cause or triggers of the patient's symptoms.

In certain instances the stent graft is of sufficient size and has more than sufficient space in order to house one or more processor circuits, CPUs, memory chips and other electrical circuits as well as antennas for sending and receiving the data. Within other embodiments, the associated medical device may be able to house the one or more processor circuits, CPUs, memory chips and other electrical circuits as well as antennas for sending and receiving the data. Processors can be programmed to collect data from the various sensors on any desired schedule as set by the medical professional. All activity can be continuously monitored post operation or post-procedure and the data collected and stored in the memory located inside the stent graft.

A patient with a stent graft will generally have regular medical checkups. When the patient goes to the doctor's office for a medical checkup, the doctor will bring a reading device closely adjacent to the stent graft, in this example the stent graft, in order to transfer the data from the internal circuit inside the stent graft to the database in the physician's office. The use of wireless transmission using smartcards or other techniques is very well known in the art and need not be described in detail. Examples of such wireless transmission of data are provided in the published patent applications and patents which have been described herein. The data which has been collected (e.g., over a short period of time, over several weeks or even several months) is transferred in a few moments from the memory which is positioned in the stent graft to the doctor's computer or wireless device. The computer therefore analyzes the data for anomalies, unexpected changes over time, positive or negative trends, and other signs which may be indicative of the health of the patient and the operability of the stent graft. For example, if the patient has decided to go skiing or jogging, the doctor will be able to monitor the effect of such activity on the stent graft, including changes during such activities. The doctor can then look at the health of the stent graft in the hours and days after the event and compare it to data prior to the event to determine if any particular event caused long term damage, or if the activities subjected the stent graft to forces beyond the manufacturer's performance specifications for that particular stent graft. Data can be collected and compared with respect to the ongoing and long term performance of the stent graft from the strain gauges, the contact sensors, the surface wear sensors, or other sensors which may be present. One representative example of an electronic data capture, documentation and clinical decision support system (EDDS) is provided in WO 2012/061825, which is incorporated by reference in its entirety.

In one alternative, the patient may also have such a reading device in their home which collates the data from the stent graft on a periodic basis, such as once per day or once per week. As described above, the patient may also be able to "trigger" a device reading (via an external signaling/triggering device) as part of "event recording." Empowering the patient to follow their own rehabilitation—and enabling them to see the positive (and negative) effects of various lifestyle choices on their health and rehabilitation—can be expected to improve compliance and improve patient outcomes. Furthermore, their experience can be shared via the web with other patients to compare their progress versus expected "norms" for function and rehabilitation and alert them to signs and symptoms that should be brought to their doctor's attention. The performance of different stent grafts can be compared in different patients (different sexes, weights, activity levels, etc.) to help manufacturers design better devices and assist surgeons and other healthcare providers in the selection of the right stent graft for specific patient types. Payers, patients, manufacturers and physicians could all benefit from the collection of this comparative information. Lastly, data accumulated at home can be collected and transmitted via the Internet to the physician's office for analysis—potentially eliminating unnecessary visits in some cases and encouraging immediate medical follow-up in others.

H. Methods of Monitoring Assemblies Comprising Stent Grafts

Figure 2:
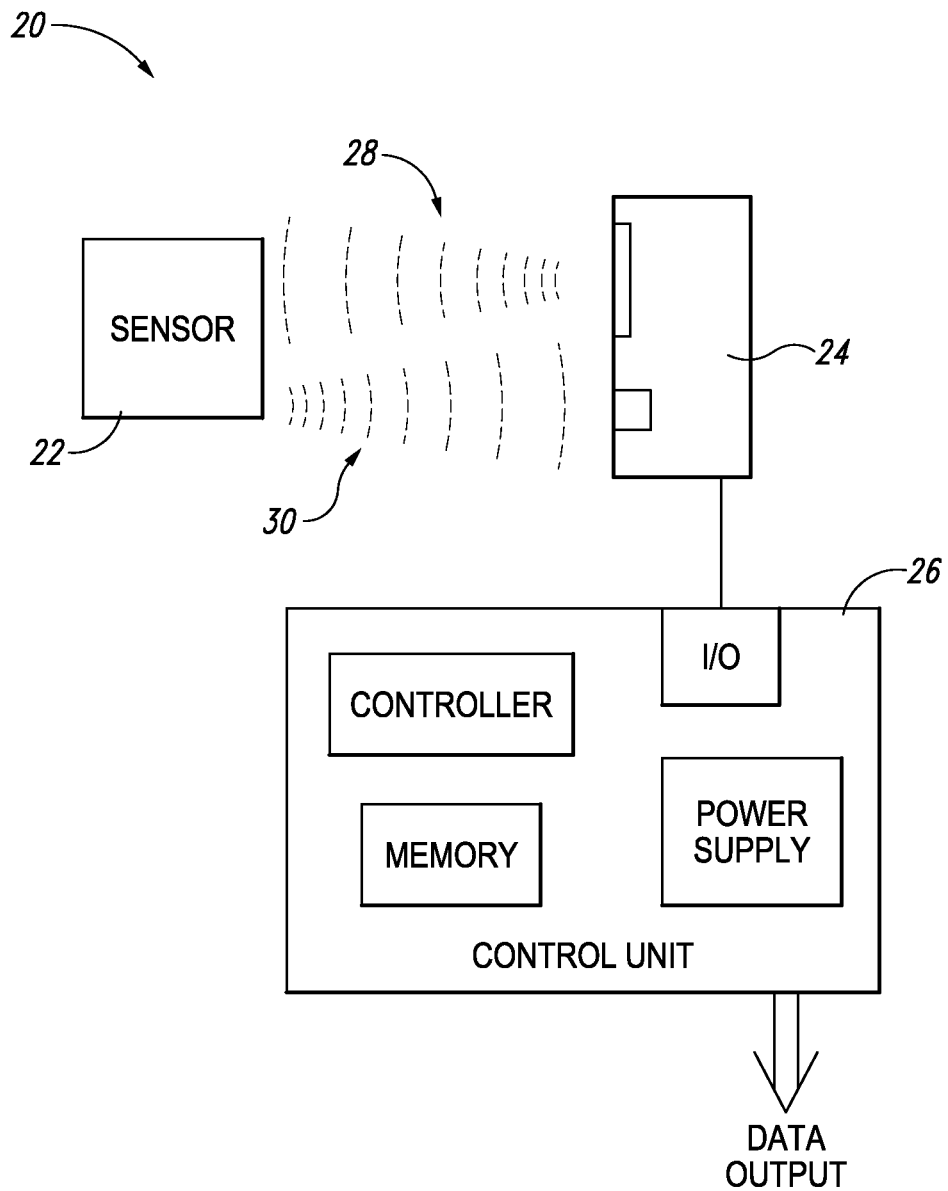
FIG. 2 is a block diagram of a sensor, interrogation module, and control unit according to one embodiment of the invention.

FIG. 2 illustrates a monitoring system 20 usable with the stent graft 14 as of the type shown in FIG. 1. The monitoring system 20 includes a sensor 22, an interrogation module 24, and a control unit 26. The sensor 22 is of the passive, wireless type which can operate on power received from a wireless source. Such sensors of this type are well known in the art and widely available. A pressure sensor of this type might be a MEMS pressure sensor, for example, Part No. LPS331AP, sold on the open market by STMicroelectronics. MEMS pressure sensors are well known to operate on very low power and suitable to remain unpowered and idle for long periods of time. They can be provided power wirelessly on an RF signal and, based on the power received wirelessly on the RF signal, perform the pressure sensing and then output the sensed data.

In one embodiment, an electrical generation system is provided that can be utilized to power the sensors described herein (including for example, fluid pressure sensors, contact sensors, position sensors, pulse pressure sensors, blood volume sensors, blood flow sensors, chemistry sensors (e.g., for blood and/or other fluids), metabolic sensors (e.g., for blood and/or other fluids), accelerometers, mechanical stress sensors, temperature sensors, and the like). For example, the electrical generation system can rely on the pulsatile blood flow throughout a vessel. After the electricity is generated by one or more generators, it can be transmitted to any one of the variety of sensors which is described herein. The transmission of the power can be carried out by any acceptable technique. For example, the generator can be directly coupled by electrical wires to one or more sensors. Alternatively (or, in addition), the electricity can be transmitted wirelessly in the same way that wireless smartcards receive power from closely adjacent power sources using the appropriate send and receive antennas.

During operation, as shown in FIG. 2, an interrogation module 24 outputs a signal 28. The signal 28 is a wireless signal, usually in the RF band, that contains power for the sensor 22 as well as an interrogation request that the sensors 22 perform a sensing. Upon being interrogated with the signal 28, the sensor 22 powers up and stores power in onboard capacitors sufficient to maintain operation during the sensing and data reporting. Such power receiving circuits and storing on onboard capacitors are well known in the art and therefore need not be shown in detail. The appropriate sensing is carried out by the sensor 22 and then the data is output from the sensor back to the interrogation module 24 on a signal 30, where it is received at an input port of the integration module.

According to one embodiment, sufficient signal strength is provided in the initial signal 28 to provide power for the sensor and to carry out the sensing operation and output the signal back to the interrogation module 24. In other embodiments, two or more signals 28 are sent, each signal providing additional power to the sensor to permit it to complete the sensing operation and then provide sufficient power to transfer the data via the signal path 30 back to the interrogation module 24. For example, the signal 28 can be sent continuously, with a sensing request component at the first part of the signal and then continued providing, either as a steady signal or pulses to provide power to operate the sensor. When the sensor is ready to output the data, it sends a signal alerting the interrogation module 24 that data is coming and the signal 28 can be turned off to avoid interference. Alternatively, the integration signal 28 can be at a first frequency and the output signal 30 at a second frequency separated sufficiently that they do not interfere with each other. In a preferred embodiment, they are both the same frequency so that the same antenna on the sensor can receive the signal 28 and send signal 30.

The interrogation signal 28 may contain data to select specific sensors on the stent. For example, the signal 28 may power up all sensors on the stent at the same time and then send requests for data from each at different selected times so that with one interrogation signal 28 provided for a set time, such as 1-2 seconds, results in each of the sensors on the stent collecting data during this time period and then, at the end of the period, reporting the data out on respective signals 30 at different times over the next 0.5 to 2 seconds so that with one interrogation signal 28, the data from all sensors 22 is collected.

The interrogation module 24 is operating under control of the control unit 26 which has a microprocessor for the controller, a memory, an I/O circuit to interface with the interrogation module and a power supply. The control unit may output data to a computer or other device for display and use by the physician to treat the patient.

Figure 3:
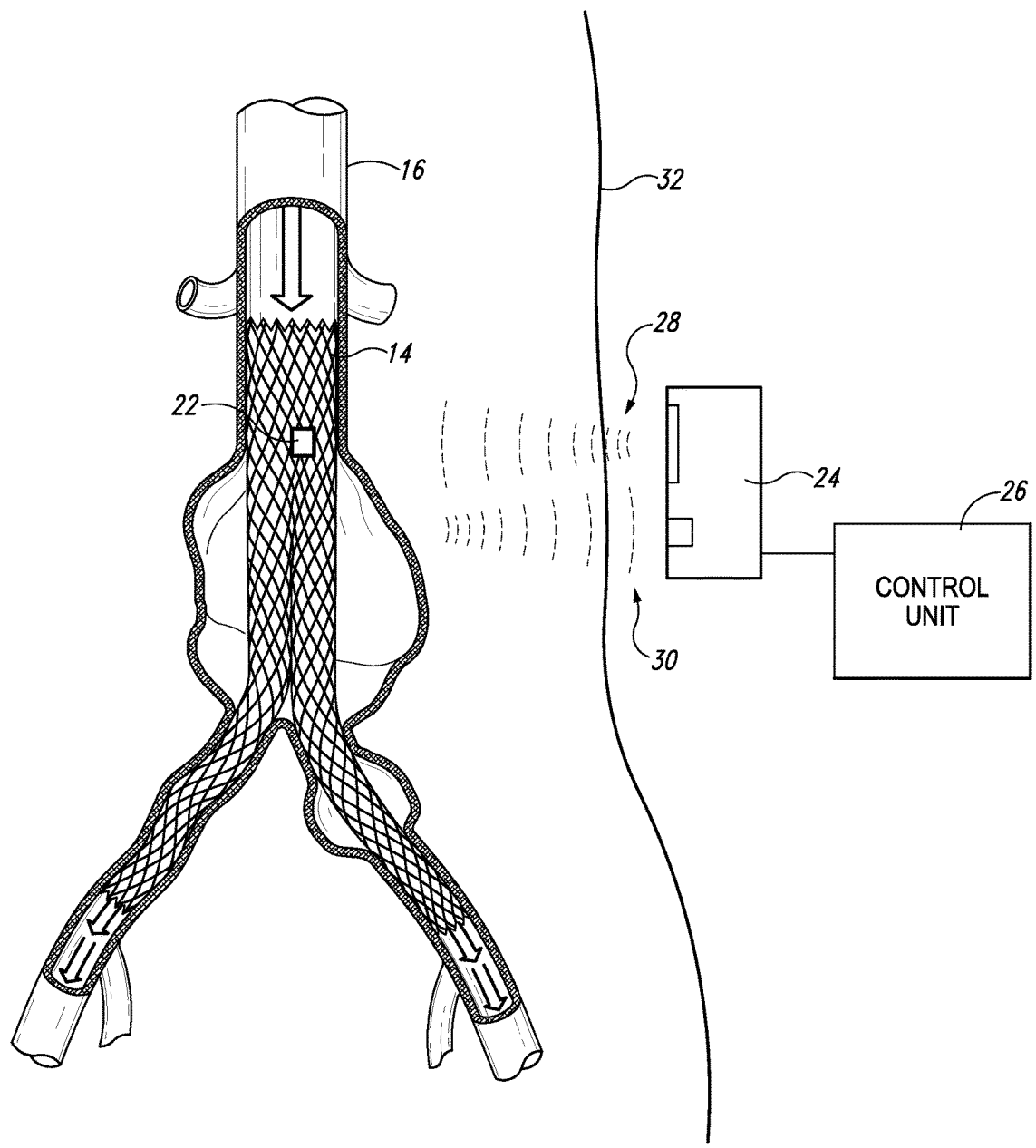
FIG. 3 is a schematic illustration of a sensor positioned on a stent graft within a patient having a sensor therein which is being probed for data and outputting data, according to one embodiment of the invention.

FIG. 3 illustrates the operation according to a preferred embodiment within a patient. The patient has an outer skin 32. The blood vessels are located inside the body of the patient. The aneurism 10 may be located at any one of number of locations in the patient. The two most common locations are in the abdominal section, near the kidneys and at the abdominal aorta and the thoracic region, adjacent to the heart. In the example shown in FIG. 3, an abdominal aortic aneurism is illustrated in which an aortic stent graft 14 has been placed in the blood vessel 16. A sensor 22 has been positioned on the stent graft. The sensor 22 may be any one of various types of sensors. For example, it may be a pressure sensor which senses the pressure of the fluid immediately adjacent the sensor on the outside wall of the sensor. Alternatively, it may be a contact sensor which senses whether there is physical contact between the blood vessel wall and the sensor itself, to confirm that the stent graft has properly sealed with the blood vessel wall. It may also be a position sensor or a location marker that provides an indication of the exact location of the stent graft within the blood vessel 16.

As illustrated in FIG. 3, the interrogation module 24 and control unit 26 are positioned outside the skin 32 of the patient. The interrogation signal 28 passes through the skin of the patient with a wireless RF signal, and the data is received on a wireless RF signal 30 from the sensor 22 back to the interrogation module 24. While the wireless signal can be in any frequency range, an RF range is preferred. A frequency in the VLF to LF ranges of between 3-300 kHz is preferred to permit the signal to be carried to sufficient depth inside the body with low power, but frequencies below 3 kHz and above 300 kHz can also be used. The sensing does not require a transfer of large amounts of data and low power is preferred; therefore, a low frequency RF signal is acceptable. This also avoids competition from and inadvertent activation by other wireless signal generators, such as blue tooth, cell phones and the like.

Figure 8:
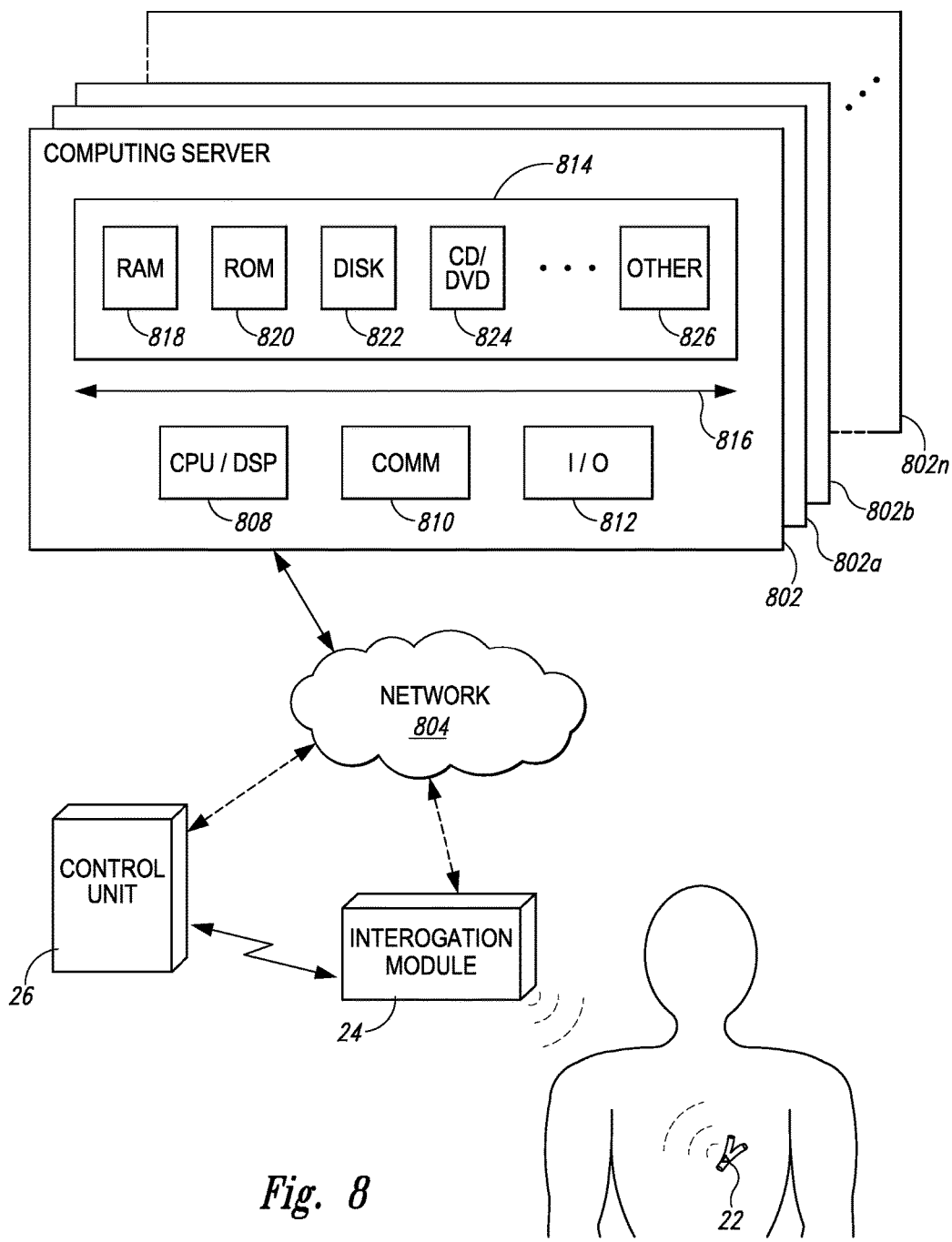
FIG. 8 illustrates an information and communication technology system embodiment arranged to process sensor data.

I. Collection, Transmission, Analysis, and Distribution of Data from Stent Graft Systems FIG. 8 illustrates one embodiment of an information and communication technology (ICT) system 800 arranged to process sensor data (e.g., data from sensor 22 of FIGS. 2 and 3). In FIG. 8, the ICT system 800 is illustrated to include computing devices that communicate via a network 804, however in other embodiments, the computing devices can communicate directly with each other or through other intervening devices, and in some cases, the computing devices do not communicate at all. The computing devices of FIG. 8 include computing servers 802, control units 26, interrogation units 24, and other devices that are not shown for simplicity.

In FIG. 8, one or more sensors 22 communicate with an interrogation module 24. The interrogation module 24 of FIG. 8 is directed by a control unit 26, but in other cases, interrogation modules 24 operates autonomously and passes information to and from sensors 22. One or both of the interrogation module 24 and control unit 26 can communicate with the computing server 802.

Within certain embodiments, the interrogation module and/or the control unit may be a wearable device on the subject. The wearable device (e.g., a watch-like device, a wrist-band, or other device that may be carried or worn by the subject) can interrogate the sensors over a set (or random) period of time, collect the data, and forward the data on to one or more networks (804). Furthermore, the wearable device may collect data of its own accord which can also be transmitted to the network. Representative examples of data that may be collected include location (e.g., a GPS), body or skin temperature, and other physiologic data (e.g., pulse). Within yet other embodiments, the wearable device may notify the subject directly of any of a number of prescribed conditions, including but not limited to possible or actual failure of the device.

The information that is communicated between an interrogation module 24 and a sensor 22 may be useful for many purposes as described herein. In some cases, for example, sensor data information is collected and analyzed expressly for the health of an individual subject. In other cases, sensor data is collected and transmitted to another computing device to be aggregated with other data (for example, the sensor data from 22 may be collected and aggregated with other data collected from a wearable device (e.g., a device that may, in certain embodiments, include GPS data and the like).

FIG. 8 illustrates aspects of a computing server 802 as a cooperative bank of servers further including computing servers 802a, 802b, and one or more other servers 802n. It is understood that computing server 802 may include any number of computing servers that operate individually or collectively to the benefit of users of the computing servers.

In some embodiments, the computing servers 802 are arranged as cloud computing devices created in one or more geographic locations, such as the United States and Canada. The cloud computing devices may be created as MICROSOFT AZURE cloud computing devices or as some other virtually accessible remote computing service.

An interrogation module 24 and a control unit 26 are optionally illustrated as communicating with a computing server 802. Via the interrogation module 24 or control unit 26, sensor data is transferred to (and in addition or alternatively from) a computing server 802 through network 804.

The network 804 includes some or all of cellular communication networks, conventional cable networks, satellite networks, fiber-optic networks, and the like configured as one or more local area networks, wide area networks, personal area networks, and any other type of computing network. In a preferred embodiment, the network 804 includes any communication hardware and software that cooperatively works to permit users of computing devices to view and interact with other computing devices.

As illustrated in FIG. 4, different types of sensors 22 may be positioned on the outer wall of the stent graft 14 in order to sense various conditions of the stent graft 14 relative to the blood vessel, and the status of the aneurism. The stent graft 14 may include one or more pressure sensors located at the proximal and distal ends of the stent graft 14, as well as within the aneurism sac in order to sense the fluid pressure at various locations along the outer wall of the stent graft 14 and within the aneurism sac. Additionally, it may include one or more contact sensors at the distal end of the stent graft 14, the proximal end of the stent graft 14, and various locations along the stent graft 14 to determine whether the stent is in physical contact with the blood vessel wall. The contact sensors may be of a type of physical pressure sensors, whereas the pressure sensors are fluid pressure sensors. In addition, one or more position markers are located on the stent graft 14 to determine whether or not it has moved relative to the blood vessel wall, since movement of the stent graft 14 is one of the conditions which causes failure. It should also be noted that the sensors 22 can also be implanted directly onto or into the aneurysm wall as part of the procedure to implant the stent graft 14 into the patient. Within related embodiments, the sensors 22 can be positioned at particular locations on or within the stent graft 14, including for example, the proximal and/or terminal one, two, or three centimeters of the device, and/or within portions of the device which are to be connected (e.g., the connecting segments of an articulating stent graft; for example, the main body 34 of a stent graft 14 and the adjoining segment arm 36).

Computing server 802 includes a central processing unit (CPU) digital signal processing unit (DSP) 808, communication modules 810, Input/Output (I/O) modules 812, and storage module 814. The components of computing server 802 are cooperatively coupled by one or more buses 816 that facilitate transmission and control of information in and through computing server 802. Communication modules 810 are configurable to pass information between the computer server 802 and other computing devices (e.g., computing servers 802a, 802b, 802n, control unit 26, interrogation unit 24, and the like). I/O modules 812 are configurable to accept input from devices such as keyboards, computer mice, trackballs, and the like. I/O modules 812 are configurable to provide output to devices such as displays, recorders, LEDs, audio devices, and the like.

Storage module 814 may include one or more types of storage media. For example, storage module 814 of FIG. 8 includes random access memory (RAM) 818, read only memory (ROM) 820, disk based memory 822, optical based memory 824, and other types of memory storage media 826. In some embodiments one or more memory devices of the storage module 814 has configured thereon one or more database structures. The database structures may be used to store data collected from sensors 22.

In some embodiments, the storage module 814 may further include one or more portions of memory organized a non-transitory computer-readable media (CRM). The CRM is configured to store computing instructions executable by a CPU 808. The computing instructions may be stored as one or more files, and each file may include one or more computer programs. A computer program can be standalone program or part of a larger computer program. Alternatively or in addition, each file may include data or other computational support material for an application that directs the collection, analysis, processing, and/or distribution of data from sensors (e.g., stent graft sensors). The sensor data application typically executes a set of instructions stored on computer-readable media.

It will be appreciated that the computing servers shown in the figures and described herein are merely illustrative and are not intended to limit the scope of the present invention. Computing server 802 may be connected to other devices that are not illustrated, including through one or more networks such as the Internet or via the Web that are incorporated into network 804. More generally, a computing system or device (e.g., a "client" or "server") or any part thereof may comprise any combination of hardware that can interact and perform the described types of functionality, optionally when programmed or otherwise configured with software, including without limitation desktop or other computers, database servers, network storage devices and other network devices, PDAs, cell phones, wireless phones, pagers, electronic organizers, Internet appliances, television-based systems (e.g., using set-top boxes and/or personal/digital video recorders), and various other products that include appropriate inter-communication capabilities. In addition, the functionality provided by the illustrated system modules may in some embodiments be combined in fewer modules or distributed in additional modules. Similarly, in some embodiments the functionality of some of the illustrated modules may not be provided and/or other additional functionality may be available.

In addition, while various items are illustrated as being stored in memory or on storage while being used, these items or portions of them can be transferred between memory and other storage devices for purposes of memory management and/or data integrity. In at least some embodiments, the illustrated modules and/or systems are software modules/systems that include software instructions which, when executed by the CPU/DSP 808 or other processor, will program the processor to automatically perform the described operations for a module/system. Alternatively, in other embodiments, some or all of the software modules and/or systems may execute in memory on another device and communicate with the illustrated computing system/device via inter-computer communication.

Furthermore, in some embodiments, some or all of the modules and/or systems may be implemented or provided in other manners, such as at least partially in firmware and/or hardware means, including, but not limited to, one or more application-specific integrated circuits (ASICs), standard integrated circuits, controllers (e.g., by executing appropriate instructions, and including microcontrollers and/or embedded controllers), field-programmable gate arrays (FPGAs), complex programmable logic devices (CPLDs), and the like. Some or all of the systems, modules, or data structures may also be stored (e.g., as software instructions or structured data) on a transitory or non-transitory computer-readable storage medium 814, such as a hard disk 822 or flash drive or other non-volatile storage device 826, volatile 818 or non-volatile memory 820, a network storage device, or a portable media article (e.g., a DVD disk, a CD disk, an optical disk, a flash memory device, etc.) to be read by an appropriate input or output system or via an appropriate connection. The systems, modules, and data structures may also in some embodiments be transmitted as generated data signals (e.g., as part of a carrier wave or other analog or digital propagated signal) on a variety of computer readable transmission mediums, including wireless-based and wired/cable-based mediums. The data signals can take a variety of forms such as part of a single or multiplexed analog signal, as multiple discrete digital packets or frames, as a discrete or streaming set of digital bits, or in some other form. Such computer program products may also take other forms in other embodiments. Accordingly, the present invention may be practiced with other computer system configurations.

In FIG. 8, sensor data from, e.g., sensor 22 is provided to computing server 802. Generally speaking, the sensor data, represents data retrieved from a known patient and from a known sensor. The sensor data may possess include or be further associated with additional information such as the USI, UDI, a time stamp, a location (e.g., GPS) stamp, a date stamp, and other information. The differences between various sensors is that some may include more or fewer data bits that associate the data with a particular source, collection device, transmission characteristic, or the like.

In some embodiments, the sensor data may comprise sensitive information such as private health information associated with a specific patient. Sensitive information, for example sensor data from sensor 22, may include any information that an associated party desires to keep from wide or easy dissemination. Sensitive information can stand alone or be combined with other non-sensitive information. For example, a patient's medical information is typically sensitive information. In some cases, the storage and transmission of a patient's medical information is protected by a government directive (e.g., law, regulation, etc.) such as the U.S. Health Insurance Portability and Accountability Act (HIPPA).

As discussed herein, a reference to "sensitive" information includes information that is entirely sensitive and information that is some combination of sensitive and non-sensitive information. The sensitive information may be represented in a data file or in some other format. As used herein, a data file that includes a patient's medical information may be referred to as "sensitive information." Other information, such as employment information, financial information, identity information, and many other types of information may also be considered sensitive information.

A computing system can represent sensitive information with an encoding algorithm (e.g., ASCII), a well-recognized file format (e.g., PDF), or by some other format. In a computing system, sensitive information can be protected from wide or easy dissemination with an encryption algorithm.

Generally speaking, sensitive information can be stored by a computing system as a discrete set of data bits. The set of data bits may be called "plaintext." Furthermore, a computing system can use an encryption process to transform plaintext using an encryption algorithm (i.e., a cipher) into a set of data bits having a highly unreadable state (i.e., cipher text). A computing system having knowledge of the encryption key used to create the cipher text can restore the information to a plaintext readable state. Accordingly, in some cases, sensitive data (e.g., sensor data 806a, 806b) is optionally encrypted before being communicated to a computing device.

In one embodiment, the operation of the information and communication technology (ICT) system 800 of FIG. 8 includes one or more sensor data computer programs stored on a computer-readable medium. The computer program may optionally direct and/or receive data from one or more stent graft sensors implanted in one or more patients. A sensor data computer program may be executed in a computing server 802. Alternatively, or in addition, a sensor data computer program may be executed in a control unit 26, an interrogation unit 24.

In one embodiment, a computer program to direct the collection and use of stent graft sensor data is stored on a non-transitory computer-readable medium in storage module 814. The computer program is configured to identify a patient who has a wireless stent graft medical devices inserted in his or her body. The wireless stent graft medical device may include one or more wireless sensor In some cases, the computer program identifies one patient, and in other cases, two or more patients are identified. The patients may each have one or more wireless stent grafts, and each wireless stent graft may have one or more wireless sensors of the type described herein.

The computer program is arranged to direct the collection of sensor data from the wireless stent graft devices. The sensor data is generally collected with a wireless interrogation unit 24. In some cases, the program communicates with the wireless interrogation unit 24. In other cases, the program communicates with a control unit 26, which in turn directs a wireless interrogation unit 24. In still other cases, some other mechanism is used direct the collection of the sensor data.

Once the sensor data is collected, the data may be further processed. For example, in some cases, the sensor data includes sensitive patient data, which can be removed or disassociated with the data. The sensor data can be individually stored (e.g., by unique sensor identification number, device number, etc.) or aggregated together with other sensor data by sensor type, time stamp, location stamp, date stamp, patient type, other patient characteristics, or by some other means.

The following pseudo-code description is used to generally illustrate one exemplary algorithm executed by a computing server 802 and generally described herein with respect to FIG. 8:

```
Start
Open a secure socket layer (SSL)
Identify a patient
Communicate with a predetermined control unit
Request sensor data from the patient via the control unit
Receive sensor data
If the sensor data is encrypted
    THEN decrypt the sensor data
Store encrypted data in the selected storage locations
Aggregate the sensor data with other sensor data
Store encrypted data in the selected storage locations
Maintain a record of the storage transaction
Perform post storage actions
End
```

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) a wired/wireless services entity (e.g., AT&T, T-Mobile); b) a communications system (e.g., a telephone system, network system, Voice over IP system); c) a device which transports individuals and/or goods from one place to another (e.g., airplanes, helicopters, cars, trucks, and trains); d) home and office appliances (e.g., refrigerators, microwaves, washing and drying machines); and (e) business which provide internet and cable access (e.g., an Internet Service Provider such as Comcast, and satellite systems such as HughesNet and VSAT Systems).

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory). Within one embodiment of the invention, a subject having a stent graft may be in one location, while processing and analysis of the data is performed in another location.

A sale of a system or method may likewise occur in a territory even if components of the system or method are located and/or used outside the territory. Further, implementation of at least part of a system for performing a method in one territory does not preclude use of the system in another territory.

In conclusion, stent grafts utilizing a variety of sensors can be utilized to serve a variety of critical clinical functions, such as safe, accurate and less traumatic placement and deployment of the stent graft, procedural and post-operative "real time" imaging of the stent graft and the surrounding anatomy, the development of stent graft complications, and the patient's overall health status. Currently, post-operative (both in hospital and out-patient) evaluation of stent graft patients is through patient history, physical examination and medical monitoring that is supplemented with diagnostic imaging studies as required. However, most of the patient's recuperative period occurs between hospital and office visits and the majority of data on daily function goes uncaptured; furthermore, monitoring patient progress through the use of some diagnostic imaging technology can be expensive, invasive and carry its own health risks (the use of nuclear isotopes or certain dyes). It can, therefore, be very difficult to accurately measure and follow the development or worsening of symptoms and evaluate "real life" stent graft performance, particularly as they relate to patient activity levels, exercise tolerance, and the effectiveness of rehabilitation efforts and medications.

At present, neither the physician nor the patient has access to the type of "real time," continuous, objective, stent graft performance measurements that they might otherwise like to have. Being able to monitor in situ stent graft function, integrity, anatomy and physiology can provide the physician with valuable objective information during office visits; furthermore, the patient can take additional readings at home at various times (e.g. when experiencing pain, during exercise, after taking medications, etc.) to provide important complementary clinical information to the doctor (which can be sent to the healthcare provider electronically even from remote locations). From the perspective of the patient, being able to monitor many of these same parameters at home allows them to take a more proactive role in their care and recovery and provide him or her with either an early warning indicator to seek medical assistance or with reassurance.

In one alternative, the patient may have a reading device in their home which collates the data from the stent graft on a periodic basis, such as once per day or once per week. In addition to empowering the patient to follow their own rehabilitation—and enabling them to see the positive (and negative) effects of various lifestyle choices on their health and rehabilitation—such information access can be expected to improve compliance and improve patient outcomes. Furthermore, their recovery experience can be shared via the web with other patients to compare their progress versus expected "norms" for function and rehabilitation and alert them to signs and symptoms that should be brought to their doctor's attention. From a public health perspective, the performance of different stent grafts can be compared in different patients (different sexes, disease severity, activity levels, concurrent diseases such as hypertension and diabetes, smoking status, obesity, etc.) to help manufacturers design better stent grafts and assist physicians in the selection of the right stent graft for a specific patient types. Payers, patients, manufacturers and physicians could all benefit from the collection of this comparative information.

Poor and dangerous products could be identified and removed from the market and objective long-term effectiveness data collected and analyzed. Lastly, data accumulated at home can be collected and transmitted via the Internet to the physician's office for analysis—potentially eliminating unnecessary visits in some cases and encouraging immediate medical follow-up in others.

The following are some specific numbered embodiments of the devices, methods and systems disclosed herein. These embodiments are exemplary only. It will be understood that the invention is not limited to the embodiments set forth herein for illustration, but embraces all such forms thereof as come within the scope of the above disclosure.

1) An assembly for positioning within a lumen comprising a stent graft; and a sensor positioned on said stent graft.

2) The assembly according to embodiment 1 wherein the sensor is positioned on an outer wall of the stent graft.

3) The assembly according to embodiment 1 wherein the sensor is positioned on an inner wall of the stent graft.

4) The assembly according to embodiment 1 wherein the sensor is positioned between the inner and outer walls of the stent graft.

5) The assembly according to embodiment 1 wherein the sensor is positioned on the luminal surface, adluminal surface, and/or implanted within the vascular wall of the aneurysm.

6) The assembly according to any one of embodiments 1 to 5 wherein the sensor is a fluid pressure sensor.

7) The assembly according to any one of embodiments 1 to 5 wherein the sensor is a contact sensor.

8) The assembly according to any one of embodiments 1 to 5 wherein the sensor is a position sensor.

9) The assembly according to any one of embodiments 1 to 5 wherein the sensor is a pulse pressure sensor.

10) The assembly according to any one of embodiments 1 to 5 wherein the sensor is a blood volume sensor 11) The assembly according to any one of embodiments 1 to 5 wherein the sensor is a blood flow sensor.

12) The assembly according to any one of embodiments 1 to 5 wherein the sensor is a blood chemistry sensor.

13) The assembly according to any one of embodiments 1 to 5 wherein the sensor is a blood metabolic sensor.

14) The assembly according to any one of embodiments 1 to 5 wherein the sensor is a mechanical stress sensor.

15) The assembly according to any one of embodiments 1 to 5 wherein said sensor is a temperature sensor.

16) The assembly according to any one of embodiments 1 to 15 wherein said stent graft is an endovascular stent graft.

17) The assembly according to any one of embodiments 1 to 16 wherein said sensor is a wireless sensor.

18) The assembly according to any one of embodiments 1 to 17 wherein said sensor is connected to a wireless microprocessor.

19) The assembly according to any one of embodiments 1 to 18 wherein a plurality of sensors are positioned on said stent graft.

20) The assembly according to any one of embodiments 1 to 19 wherein said stent graft comprises more than one type of sensor.

21) The assembly according to any one of embodiments 1 to 20 wherein said stent graft comprises one or more fluid pressure sensors, contact sensors and position sensors.

22) The assembly according to any one of embodiments 1 to 21 wherein said sensor is a plurality of sensors which are positioned on said stent graft at a density of greater than 1 sensor per square centimeter.

23) The assembly according to any one of embodiments 1 to 22 wherein said sensor is a plurality of sensors which are positioned on said stent graft at a density of greater than 2 sensors per square centimeter on an end of said stent graft.

24) The assembly according to any one of embodiments 1 to 23 wherein said sensor has a unique sensor identification number.

25) The assembly according to any one of embodiments 1 to 24 wherein said sensor is uniquely defined within a specific position on said stent graft.

26) The assembly according to any one of embodiments 1 to 25 wherein said stent graft has a density of sensors of grater 2, 3, 4, 5, 6, 7, 8, 9 or 10 sensors per square centimeter of the stent graft.

27) The assembly according to any one of embodiments 1 to 26 wherein said stent graft has a density of sensors of grater 2, 3, 4, 5, 6, 7, 8, 9 or 10 sensors per cubic centimeter of the stent graft.

28) The assembly according to anyone of embodiments 1 to 27 wherein said stent graft is comprised of two segments, and wherein contact sensors on each of said two segments sense joining of said two segments.

29) An assembly comprising a stent graft and a sensor, wherein said sensor measures the cardiac output of a subject.

30) An assembly comprising a stent graft and a sensor, wherein said sensor measures the stroke volume of a subject.

31) An assembly comprising a stent graft and a sensor, wherein said sensor measures the ejection fraction of a subject.

32) An assembly comprising a stent graft and a sensor, wherein said sensor measures the systolic blood pressure of a subject.

33) An assembly comprising a stent graft and a sensor, wherein said sensor measures the diastolic blood pressure of a subject.

34) An assembly comprising a stent graft and a sensor, wherein said sensor measures the mean arterial pressure of a subject.

35) An assembly comprising a stent graft and a sensor, wherein said sensor measures the systemic vascular resistance of a subject.

36) An assembly comprising a stent graft and a sensor, wherein said sensor measures the total peripheral resistance of a subject.

37) An assembly comprising a stent graft and a sensor, wherein said sensor measures the temperature of a subject.

38) Use of a stent graft according to any one of embodiments 1 to 37 to measure the development of, or occurrence of, a type I, II, III, IV or V endoleak.

39) Use of a stent graft according to any one of embodiments 1 to 37 to obtain a measurement of cardiac function.

40) The use according to embodiment 39 wherein said measurement of cardiac function is selected from the group consisting of cardiac output, stroke volume, ejection fraction, systolic and/or diastolic blood pressure, mean arterial pressure, systemic vascular resistance, and total peripheral resistance.

41) Use according to any one of embodiments 38 to 40, wherein said measurement occurs at more than one time point.

42) Use according to any one of embodiments 38 to 41, wherein said measurement takes place over more than 1, 2, 3, 4, 5, 10, 15, or 30 days.

43) Use according to any one of embodiments 38 to 42, wherein said measurement takes place over more than 1, 2, 3, 4, 6 or 12 months.

44) A method of monitoring a stent graft comprising:
transmitting a wireless electrical signal from a location outside the body to a location inside the body;
receiving the signal at a sensor positioned on a stent graft located inside the body; powering the sensor using the received signal;
sensing data at the sensor; and
outputting the sensed data from the sensor to a receiving unit located outside of the body.

45) The method of embodiment 44, wherein said sensor positioned on a stent graft is an assembly according to any one of embodiments 1 to 37.

46) The method according to embodiments 44 or 45 wherein said receiving unit is a watch, wrist band, cell phone, or glasses 47) The method according to embodiments 44 or 45 wherein said receiving unit is located within a subject's residence or office.

48) The method according to any one of embodiments 44 to 46 wherein said sensed data is provided to a health care provider.

49) A non-transitory computer-readable storage medium whose stored contents configure a computing system to perform a method, the method comprising:
identifying a patient, the identified patient having at least one wireless stent graft, each wireless stent graft having one or more wireless sensors;
directing a wireless interrogation unit to collect sensor data from at least one of the respective one or more wireless sensors; and
receiving the collected sensor data.

50) The non-transitory computer-readable storage medium of embodiment 49 whose stored contents configure a computing system to perform a method, the method further comprising:
identifying a plurality of patients, each identified patient having at least one wireless stent graft, each wireless stent graft having one or more wireless sensors;
directing a wireless interrogation unit associated with each identified patient to collect sensor data from at least one of the respective one or more wireless sensors; receiving the collected sensor data; and
aggregating the collected sensor data.

51) The non-transitory computer-readable storage medium of embodiment 50 whose stored contents configure a computing system to perform a method, the method further comprising:
removing sensitive patient data from the collected sensor data; and
parsing the aggregated data according to a type of sensor.

52) The non-transitory computer-readable storage medium of embodiment 50 whose stored contents configure a computing system to perform a method, wherein directing the wireless interrogation unit includes directing a control unit associated with the wireless interrogation unit.

53) The method according to any one of embodiments 50 to 52, wherein said sensor positioned on a stent graft is an assembly according to any one of embodiments 1 to 37.

54) The method according to any one of embodiments 50 to 53 wherein said receiving is performed by a watch, wrist band, cell phone, or glasses 55) The method according to any one of embodiments 50 to 53 wherein said receiving is performed within a subject's residence or office.

56) The method according to any one of embodiments 50 to 55 wherein said collected sensed data is provided to a health care provider.

57) The method of any one of embodiments 50 to 56, further comprising the step of analyzing the collected sensor data.

58) The method according to embodiment 57 wherein said collected data is analyzed for similarity, dissimilarity, and trends of one or more of the following: (a) subject sex, (b) subject age, (c) subject race; (d) subject's genomic information; (e) subject health, (f) stent graft manufacture, (g) stent graft type; (h) stent graft model number; (i) implanting hospital or clinic; and (j) implanting physician.

59) A method for detecting infection within a subject having an implanted assembly according to any one of embodiments 1 to 37, comprising: (a) detecting temperature on, within or around said stent graft; and (b) determining whether said temperature increases over time.

60) A method for placing a stent graft with one or more sensors into a subject, comprising: (a) implanting a first portion of a stent graft having a first set of one or more contact sensors into a subject; implanting a second connecting portion of a stent graft having a second set of one or more contact sensors into a subject; wherein said first and second set of contact sensors are utilized to properly place said stent graft.

61) The method according to embodiment 60 wherein said first portion of a stent graft and second connecting portion of a stent graft have one or more additional sensors selected from the group consisting of a fluid pressure sensor, contact sensor, position sensor, pulse pressure sensor, blood volume sensor, blood flow sensor, blood chemistry sensor, blood metabolic sensor, mechanical stress sensor, and a temperature sensor.

62) The method according to embodiment 60 wherein said properly placed stent graft is an assembly according to any one of embodiments 1 to 37.

63) A method for detecting changes in a stent graft, comprising the steps of (a) collecting data from a sensor at a first point; (b) collecting data from said sensor at least a second point; and (c) determining whether there was a change in data from said first point to said second point.

64) The method according to embodiment 63, wherein multiple collections of data are taken over a period of time selected from the group consisting of seconds, minutes, hours, days, months and years.

65) The method according to embodiment 63 or 64 wherein said stent graft is an assembly according to any one of embodiments 1 to 37.

66) The method according to any one of embodiments 63 to 65, further comprising the step of analyzing said collected data.

67) The method according to any one of embodiments 63 to 66, wherein said data is plotted to enable visualization of change over time.

68) The method according to any one of embodiments 63 to 67, wherein said data is plotted to provide a three-dimensional image of said stent graft.

69) The method according to any one of embodiments 63 to 68, wherein said data is analyzed to determine the presence or absence of an endoleak.

70) The method according to embodiment 69 wherein said endoleak is a type I, II, III, IV, or V endoleak.

71) The method according to any one of embodiments 63 to 68 wherein said data is analyzed to determine the presence or absence of an infection.

72) The various embodiments described above can be combined to provide further embodiments. All of the U.S. patents, U.S. patent application publications, U.S. patent applications, foreign patents, foreign patent applications and non-patent publications referred to in this specification are incorporated herein by reference, in their entirety. Aspects of the embodiments can be modified, if necessary to employ concepts of the various patents, applications and publications to provide yet further embodiments.

73) In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An assembly comprising a stent graft and a sensor, wherein the stent graft comprises a stent and a graft, and the sensor measures at least one a subject's cardiac output, stroke volume, ejection fraction, systolic blood pressure, diastolic blood pressure, mean arterial pressure, systemic vascular resistance, and total peripheral resistance and wherein the stent graft is further comprised of two segments and contact sensors are located on each of the two segments, and wherein the contact sensors on each of the two segments sense joining of the two segments.

2. The assembly of claim 1 wherein the sensor is a fluid pressure sensor.

3. The assembly of claim 1 further comprising a position sensor.

4. The assembly of claim 1 wherein the sensor is a pulse pressure sensor.

5. The assembly of claim 1 wherein the sensor is a blood volume sensor.

6. The assembly of claim 1 wherein the sensor is a blood flow sensor.

7. The assembly of claim 1 further comprising a blood chemistry sensor.

8. The assembly of claim 1 further comprising a blood metabolic sensor.

9. The assembly of claim 1 further comprising a mechanical stress sensor.

10. The assembly of claim 1 wherein the sensor is a temperature sensor.

11. The assembly of claim 1 wherein the stent graft is an endovascular stent graft.

12. The assembly of claim 1 wherein the sensor is a wireless sensor.

13. The assembly of claim 1 wherein the sensor is connected to a wireless microprocessor.

14. The assembly of claim 1 wherein a plurality of sensors are positioned on the stent graft.

15. The assembly of claim 1 wherein the sensor has a unique sensor identification number.

16. The assembly of claim 1 wherein the sensor is uniquely defined within a specific position on the stent graft.

17. The assembly of claim 1 wherein the stent graft has a density of sensors of 1-10 sensors per square centimeter of the stent graft.

18. The assembly of claim 1 wherein the stent graft has a density of sensors of 1-10 sensors per cubic centimeter of the stent graft.

* * * * *